United States Patent
Masliah et al.

(10) Patent No.: US 8,450,481 B2
(45) Date of Patent: May 28, 2013

(54) COMPOUNDS FOR INHIBITING PROTEIN AGGREGATION, AND METHODS FOR MAKING AND USING THEM

(75) Inventors: Eliezer Masliah, San Diego, CA (US); Igor Tsigelny, San Diego, CA (US); Wolfgang Wrasidlo, La Jolla, CA (US); Edward Rockenstein, Chula Vista, CA (US)

(73) Assignee: The Regents of the University of California, Oakland, CA (US)

( * ) Notice: Subject to any disclaimer, the term of this patent is extended or adjusted under 35 U.S.C. 154(b) by 456 days.

(21) Appl. No.: 12/602,689

(22) PCT Filed: Jun. 13, 2008

(86) PCT No.: PCT/US2008/067011
§ 371 (c)(1),
(2), (4) Date: May 20, 2010

(87) PCT Pub. No.: WO2008/157425
PCT Pub. Date: Dec. 24, 2008

(65) Prior Publication Data
US 2010/0226969 A1    Sep. 9, 2010

Related U.S. Application Data

(60) Provisional application No. 60/944,070, filed on Jun. 14, 2007.

(51) Int. Cl.
*C07D 417/04* (2006.01)
*A61K 9/127* (2006.01)
*A61K 31/4985* (2006.01)

(52) U.S. Cl.
USPC .................. 544/279; 424/450; 514/249

(58) Field of Classification Search
USPC ................. 544/279; 424/450; 514/249
See application file for complete search history.

(56) References Cited

U.S. PATENT DOCUMENTS

| | | | |
|---|---|---|---|
| 5,034,051 A | | 7/1991 | Kume et al. |
| 5,929,237 A | * | 7/1999 | Kahn ................. 544/279 |
| 5,994,376 A | | 11/1999 | Freyne et al. |
| 6,403,805 B1 | | 6/2002 | Freyne et al. |
| 6,780,971 B2 | | 8/2004 | Wolozin et al. |

FOREIGN PATENT DOCUMENTS
WO    WO 2005/090319    9/2005

OTHER PUBLICATIONS

Yun-Kyung Kim, Mar. 12, 2009, WO/2008/157425 A3 Later publication of international search report, KIPO, ISA/KR, WIPO.
Ellen Moyse, Dec. 17, 2009, PCT/US2008/067011 International Preliminary Report on Patentability Chapter I, WIPO.
Un-Kyung Kim, Mar. 12, 2009, PCT/US2008/067011 Written Opinion of the International Search Authority, KIPO, ISA/KR, WIPO.

* cited by examiner

*Primary Examiner* — Joseph Kosack
(74) *Attorney, Agent, or Firm* — Gregory P. Einhorn; Gavrilovich, Dodd & Lindsey LLP

(57) ABSTRACT

The invention provides compositions comprising protein aggregation inhibitors, and pharmaceutical compositions comprising them, and methods for making and using them, including methods for preventing, reversing, slowing or inhibiting protein aggregation, e.g., for treating diseases that are characterized by protein aggregation—including some degenerative neurological diseases such as Parkinson's disease. In one aspect, the compositions of the invention specifically target synuclein, beta-amyloid and/or tau protein aggregates, and the methods of the invention can be used to specifically prevent, reverse, slow or inhibit synuclein, beta-amyloid and/or tau protein aggregation. In alternative embodiments, the compositions and methods of the invention, are used to treat, prevent or ameliorate (including slowing the progression of) degenerative neurological diseases related to or caused by protein aggregation, e.g., synuclein, beta-amyloid and/or tau protein aggregation. In one aspect, compositions and methods of this invention are used to treat, prevent or ameliorate (including slowing the progression of) Parkinson's disease, Alzheimer's Disease (AD), Lewy body disease (LBD) and Multiple system atrophy (MSA).

13 Claims, 21 Drawing Sheets

Bicyclic peptido scaffolds for alpha-synnulein inhibitors pyrimido

FIGURE 13B
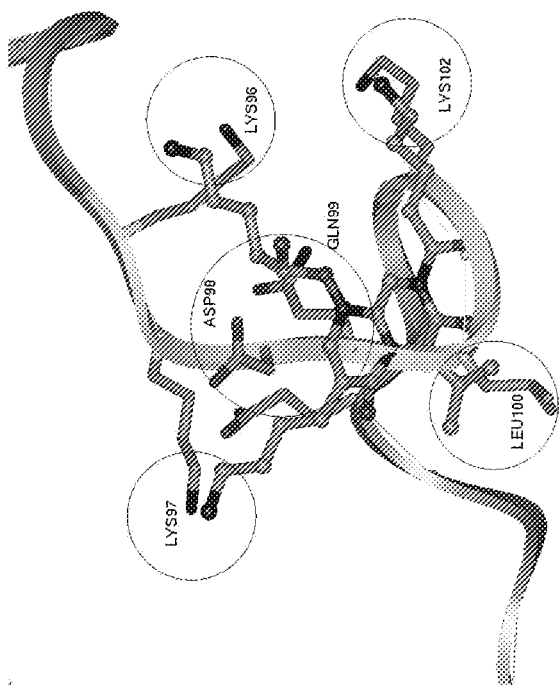
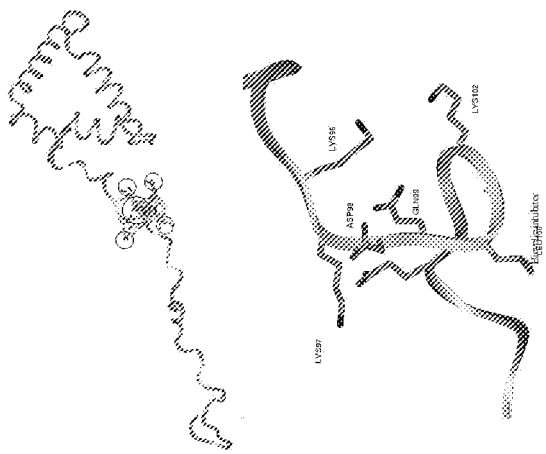
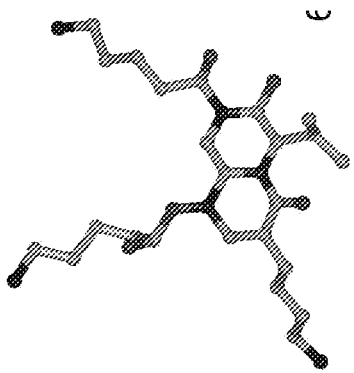
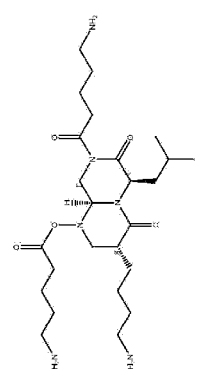
Compound in SAI

*J. Org. Chem.* 63, 1998, 1248.

Chemical Formula: $C_{24}H_{36}N_8O_6$
Exact Mass: 532.28
Molecular Weight: 532.59
m/z: 532.28 (100.0%), 533.28 (26.6%), 534.28 (5.3%), 533.27 (3.0%)
Elemental Analysis: C, 54.12; H, 6.81; N, 21.04; O, 18.02

Log P: 0.41
MR: 141.18 [cm3/mol]
Henry's Law: 27.26
Heat of Form: -401.75 [kJ/mol]
tPSA: 160.78
CLogP: -0.377919
CMR: 14.0874 under US 8,450,481 B2

COMPOUNDS FOR INHIBITING PROTEIN AGGREGATION, AND METHODS FOR MAKING AND USING THEM

This invention was made with government support under AG18440 awarded by the National Institute of Health. The government has certain rights in the invention.

TECHNICAL FIELD

This invention generally relates to protein chemistry, cell biology, neuroscience and medicine. The invention provides compositions comprising protein aggregation inhibitors, and pharmaceutical compositions comprising them, and methods for making and using them, including methods for preventing, reversing, slowing or inhibiting protein aggregation, e.g., for treating diseases that are characterized by protein aggregation—including some degenerative neurological diseases such as Parkinson's disease, Alzheimer's Disease (AD), Lewy body disease (LBD) and Multiple system atrophy (MSA). In one aspect, the compositions of the invention specifically target synuclein, beta-amyloid and/or tau protein aggregates, and the methods of the invention can be used to specifically prevent, reverse, slow or inhibit synuclein, beta-amyloid and/or tau protein aggregation.

In alternative embodiments, the compositions and methods of the invention, including the synuclein, beta-amyloid and/or tau protein aggregation inhibiting compositions of the invention, and the pharmaceutical compositions comprising them, are used to treat, prevent or ameliorate (including slowing the progression of) degenerative neurological diseases related to or caused by protein aggregation, e.g., synuclein, beta-amyloid and/or tau protein aggregation. In one aspect, compositions and methods of this invention are used to treat, prevent or ameliorate (including slowing the progression of) Parkinson's disease, Alzheimer's Disease (AD), Lewy body disease (LBD) and Multiple system atrophy (MSA).

BACKGROUND

Abnormal accumulation of alpha-synuclein (SYN) in the nervous system results in progressive damage to neurons leading to Parkinson's Disease (PD). The SYN molecule also has been shown to aggregate and promote nerve cell damage in other neurological disorders including Alzheimer's Disease (AD), Lewy body disease (LBD) and Multiple system atrophy (MSA). SYN is a 140 amino acid (aa) nerve terminal molecule involved in synaptic plasticity and dopamine release.

Proteins and peptides that function as chaperone molecules or that have some homology with SYN (e.g.: HSP-70 and beta-synuclein) and small compounds (e.g.: Rifampicin and flavinoids) have been described to block SYN aggregation and fibrillation.

SUMMARY

The invention provides compositions comprising protein aggregation inhibitors, and pharmaceutical compositions comprising them, and methods for making and using them, including methods for preventing, reversing, slowing or inhibiting protein aggregation, e.g., for treating diseases that are characterized by protein aggregation—including some degenerative neurological diseases and conditions, such as Parkinson's disease, Alzheimer's Disease (AD), Lewy body disease (LBD) and Multiple system atrophy (MSA). In one aspect, the compositions of the invention specifically target synuclein, beta-amyloid and/or tau protein aggregates, and the methods of the invention can be used to specifically prevent, reverse, slow or inhibit synuclein, beta-amyloid and/or tau protein aggregation.

In alternative embodiments, the compositions and methods of the invention, including the synuclein, beta-amyloid and/or tau protein aggregation inhibiting (including aggregation-preventing, or aggregation-reversing) compositions of the invention, and the pharmaceutical compositions comprising them, are used to treat, prevent or ameliorate (including slowing the progression of) degenerative neurological diseases related to or caused by aggregation, e.g., synuclein, beta-amyloid and/or tau protein aggregation. In one aspect, compositions and methods of this invention are used to treat, prevent or ameliorate (including slowing the progression of) Parkinson's disease, Alzheimer's Disease (AD), Lewy body disease (LBD) and Multiple system atrophy (MSA).

In alternative embodiments, compounds of the invention (which include analog compositions of the invention) comprise/consist of (are) compounds having a formula as set forth in FIG. 8; wherein in alternative embodiments $R_1$, $R_2$, $R_3$ and/or the $R_4$ group(s) are independently selected from the group consisting of hydrogen, halo, hydroxy (—OH), thiol (—SH), cyano (—CN), formyl (—CHO), alkyl, haloalkyl, alkene, alkenyl, alkynyl, heteroalkyl, heteroalkenyl, heteroalkynyl, aryl, substituted aryl, amino, nitro (—NO$_2$), alkoxy, haloalkoxy, thioalkoxy, alkanoyl, haloalkanoyl and carbonyloxy; (b) the formula of (a), wherein the alkyl, haloalkyl, alkene, alkenyl in both or either of the $R_1$, $R_2$, $R_3$ and/or the $R_4$ group(s) are at least 1, 2, 3, 4, 5, 6, 7, 8, 9, 10, 11, 12, 13, 14, 15 or 16 or more carbons in length; (c) the formula of (a) or (b), wherein the heterocyclic moiety comprises a 5 membered ring or a 6 membered ring system; or (d) the formula of (c), wherein 5 membered ring system comprises an imidazole, thiazole, triazole or oxadiazole, or the 6 membered ring system comprises a pyridine, a pyrimidine or a pyrazine.

The invention provides isolated, synthetic or recombinant polypeptides or peptides comprising:
  (a) an amino acid sequence comprising, or consisting of, at least 85%, 86%, 87%, 88%, 89%, 90%, 91%, 92%, 93%, 94%, 95%, 96%, 97%, 98%, 99%, or more or complete (100%) sequence identity to (i) KKDQLGK (SEQ ID NO:1), or (ii) EKTKEQVTN (SEQ ID NO:2);
  (b) an amino acid sequence comprising, or consisting of: (i) between 5 and 7 consecutive residues of the polypeptide or peptide of the amino acid sequence (a) or KKDQLGK (SEQ ID NO:1); or, (ii) between 5 and 9 consecutive residues of the amino acid sequence (a) or EKTKEQVTN (SEQ ID NO:2);
  (c) the polypeptide or peptide of (a) or (b), and having one or more amino acid residue deletions or conservative amino acid substitutions;
  (d) the polypeptide or peptide of (c), wherein the one or more conservative amino acid substitution comprises substituting an amino acid with another amino acid of like characteristics; or, a conservative substitution comprises: replacement of an aliphatic amino acid with another aliphatic amino acid; replacement of a serine with a threonine or vice versa; replacement of an acidic residue with another acidic residue; replacement of a residue bearing an amide group with another residue bearing an amide group; exchange of a basic residue with another basic residue; or replacement of an aromatic residue with another aromatic residue;

(e) the polypeptide or peptide of any of (a) to (d), and having between one and nine amino acid residue changes based on KKDQLGK (SEQ ID NO:1) or EKTKEQVTN (SEQ ID NO:2);
(f) the polypeptide or peptide of any of (a) to (e), wherein the polypeptide or peptide can inhibit protein aggregation;
(g) the polypeptide or peptide of (f), wherein the polypeptide or peptide can inhibit protein aggregation of a protein comprising or consisting of a synuclein, a beta-amyloid or a tao protein;
(h) the polypeptide or peptide of any of (a) to (g), wherein the polypeptide or peptide chemically synthesized or is recombinantly produced;
(i) the polypeptide or peptide of any of (a) to (h), further comprising a heterologous protein or a non-protein moiety;
(j) the polypeptide or peptide of (i), wherein the polypeptide or peptide is conjugated to a carrier;
(k) the polypeptide or peptide of (j), wherein the carrier comprises or consists of a poly-Arg, a TAT or a *Drosophila antennapedia* homeodomain; or
(l) the polypeptide or peptide of any of (a) to (k), further comprising at least one pharmaceutically acceptable excipient.

The invention provides compounds comprising or consisting of:
(a) formula (I),

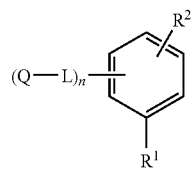

wherein $R^1$ is selected from a group comprising C1-C6 alkyl, C1-C6 aminoalkyl, C2-C12 heteroalkyl, C2-C6 alkenyl and C2-C6 alkynyl;
$R^2$ is H, O(C=O)NR'Z($R^3$)$_n$ or NR'(C=O)OZ($R^3$)$_n$, wherein $R^3$ is H, C1-C6 aminoalkyl or NR'$_2$;
each Z is independently a 5-6 membered aromatic or heteroaromatic ring;
each n is independently 1 or 2;
each L is independently selected from a group comprising a bond, O, C2-C12 alkylene and C2-C12 heteroalkylene, wherein each alkylene is optionally substituted with C1-C6 aminoalkyl;
each Q is independently H or a 5-6 membered unsaturated heterocyclic ring containing at least one N or S as a ring member, wherein each ring is independently substituted with at least one member of the group comprising C1-C6 aminoalkyl, =O, C4-C12 alkylheterocycloalkyl, C1-C4 alkyl, NR'$_2$;
each R' is independently selected from the group comprising H, C1-C4 alkyl, C2-C4 alkenyl and C2-C4 alkynyl;
(b) a pharmaceutically acceptable salt of the compound of (a); or
(c) the compound of (a) or (b), further comprising a heterologous polypeptide or peptide or a non-protein moiety;
(d) the compound of (c), wherein the compound, and/or the polypeptide or peptide, is conjugated to a carrier;
(e) the compound of (d), wherein the carrier comprises or consists of a poly-Arg, a TAT or a *Drosophila antennapedia* homeodomain; or
(f) the compound of any of (a) to (e), further comprising at least one pharmaceutically acceptable excipient.

In one aspect of this compound of the invention:
(a) $R^1$ is selected from a group consisting of C1-C4 alkyl, C1-C4 aminoalkyl and O(C1-C4 alkylene)OC1-C4 alkyl,
and each L is independently selected from a group comprising a bond, O and O(C1-C4 alkylene)O(C1-C4 alkylene), wherein each alkylene is optionally substituted with C1-C4 aminoalkyl;
(b) Q is selected from a group consisting of pyrrolyl, pyrazolyl, imidazolyl, triazolyl, thiophenyl, thiazolyl, isothiazolyl and thiadiazolyl; and Z is phenyl, or Q is imidazolyl or thiazolyl; or
(c) at least any one of $R^1$ or $R^3$ is C1-C6 aminoalkyl, or
any L is C2-C12 alkylene or C2-C12 heteroalkylene, further substituted with C1-C6 aminoalkyl, or
any Q is a 5-6 membered unsaturated ring further substituted with C1-C6 aminoalkyl.

The invention provides compounds comprising or consisting of:
(a) formula (II)

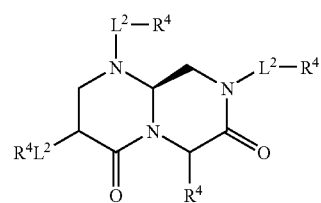

wherein each $L^2$ is independently selected from a group consisting of a bond, SO$_2$, SO$_2$NH, CO$_2$NH, (C=O)NH, (C=O)NHNH(C=O), C=O, O(C=O), (C=O)O and C1-C22 alkylene,
each $R^4$ is independently selected from a group consisting of H, C1-C6 aminoalkyl, C2-C6 aminoalkenyl, C2-C6 aminoalkynyl, C1-C6 alkyl, C2-C6 alkenyl, C2-C6 alkynyl and 5-6 membered aromatic ring;
(b) the compound of (a), wherein at least one $R^4$ is a C1-C6 aminoalkyl;
(c) a pharmaceutically acceptable salt of the compound of (a) or (b);
(d) the compound of any of (a) to (c), further comprising a heterologous polypeptide or peptide or a non-protein moiety;
(e) the compound of (d), wherein the compound, and/or the polypeptide or peptide, is conjugated to a carrier;
(f) the compound of (e), wherein the carrier comprises or consists of a poly-Arg, a TAT or a *Drosophila antennapedia* homeodomain; or
(g) the compound of any of (a) to (f), further comprising at least one pharmaceutically acceptable excipient.

The invention provides compounds comprising or consisting of:
(a) formula (III),

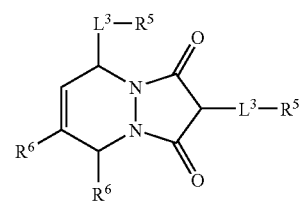

wherein each $L^3$ is independently selected from the group consisting of a bond, NH(C=O), C=O, O(C=O), (C=O)O and (C=O)NH;

each R⁵ is independently selected from the group consisting of H, C1-C6 aminoalkyl, C2-C6 aminoalkenyl, and C2-C6 aminoalkynyl; and each R⁶ is independently selected from the group consisting of C1-C6 alkyl, C2-C6 alkenyl and C2-C6 alkynyl;

(b) compound of (a), wherein at least any one of R⁵ or R⁶ is C1-C6 aminoalkyl;

(c) a pharmaceutically acceptable salt of the compound of (a) or (b);

(d) the compound of any of (a) to (c), further comprising a heterologous polypeptide or peptide or a non-protein moiety;

(e) the compound of (d), wherein the compound, and/or the polypeptide or peptide, is conjugated to a carrier;

(f) the compound of (e), wherein the carrier comprises or consists of a poly-Arg, a TAT or a *Drosophila antennapedia* homeodomain; or (g) the compound of any of (a) to (f), further comprising at least one pharmaceutically acceptable excipient.

The invention provides compounds comprising or consisting of:

(a) formula (IV),

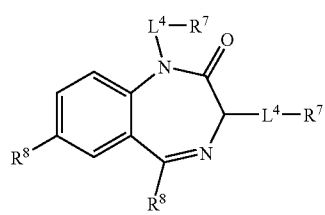

(IV)

wherein each L⁴ is independently selected from the group consisting of a bond, C=O, NH(C=O), O(C=O), (C=O)NH, and (C=O)O;

each R⁷ is independently selected from the group consisting of H, C1-C6 aminoalkyl, C2-C6 aminoalkenyl and C2-C6 aminoalkynyl; and each R⁸ is independently selected from the group consisting of H, C1-C6 alkyl, C2-C6 alkenyl, and C2-C6 alkynyl;

(b) the compound of (a), wherein at least any one of R⁷ or R⁸ is C1-C6 aminoalkyl;

(c) a pharmaceutically acceptable salt of the compound of (a) or (b);

(d) the compound of any of (a) to (c), further comprising a heterologous polypeptide or peptide or a non-protein moiety;

(e) the compound of (d), wherein the compound, and/or the polypeptide or peptide, is conjugated to a carrier;

(f) the compound of (e), wherein the carrier comprises or consists of a poly-Arg, a TAT or a *Drosophila antennapedia* homeodomain; or (g) the compound of any of (a) to (f), further comprising at least one pharmaceutically acceptable excipient.

The invention provides compounds comprising or consisting of:

(a) formula (V),

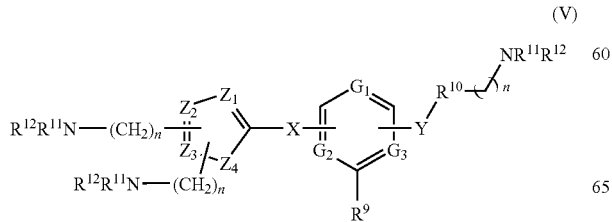

(V)

wherein each X and Y are independently O, S, NH, NR¹³, or CH₂;

Z¹, Z², Z³, Z⁴ are independently CH, O, S, N or NH;

R¹⁰ is phenyl or a 5-6 membered heterocyclic ring, further optionally substituted with Z¹, Z², Z³, Z⁴;

G¹, G², G³ are independently CH, N or C=O;

R¹¹ and R¹² are independently H or a cycloalkyl ring;

n is 1-18;

R¹³ is CONH₂, COOH, SO₂NH₂, SO₂alkyl; and

R⁹ is C1-C18 alkyl or an aryl group;

(b) the compound of (a), wherein at least any one of R¹¹ or R¹² is C1-C6 aminoalkyl;

(c) a pharmaceutically acceptable salt of the compound of (a) or (b);

(d) the compound of any of (a) to (c), further comprising a heterologous polypeptide or peptide or a non-protein moiety;

(e) the compound of (d), wherein the compound, and/or the polypeptide or peptide, is conjugated to a carrier;

(f) the compound of (e), wherein the carrier comprises or consists of a poly-Arg, a TAT or a *Drosophila antennapedia* homeodomain; or (g) the compound of any of (a) to (f), further comprising at least one pharmaceutically acceptable excipient.

The invention provides compounds comprising or consisting of:

(a) formula selected from the group consisting of

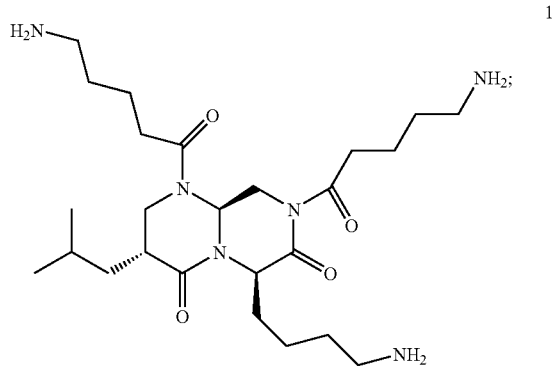

1

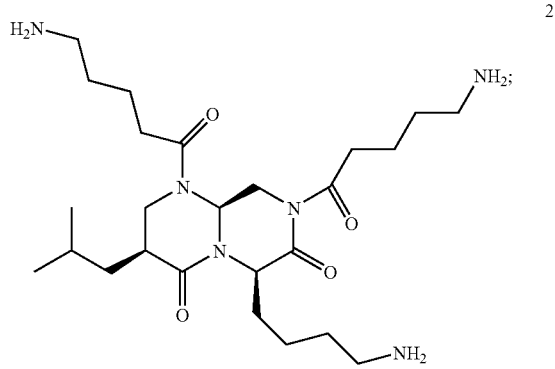

2

-continued
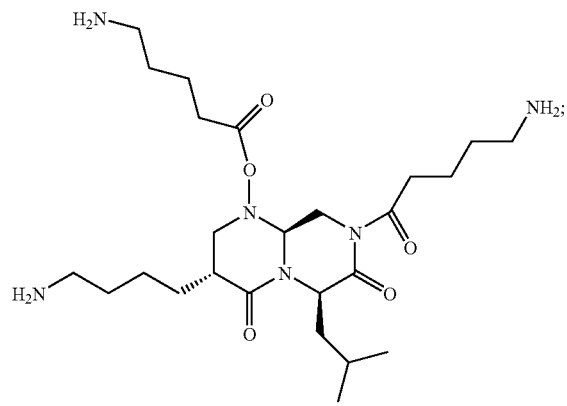
3
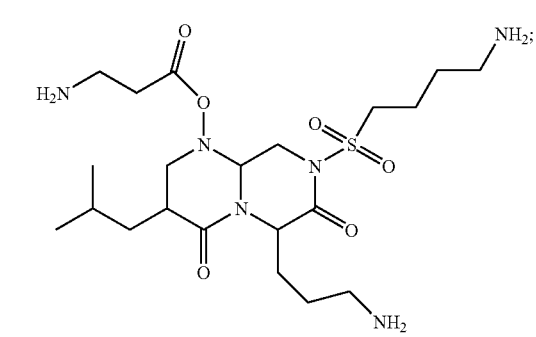
4
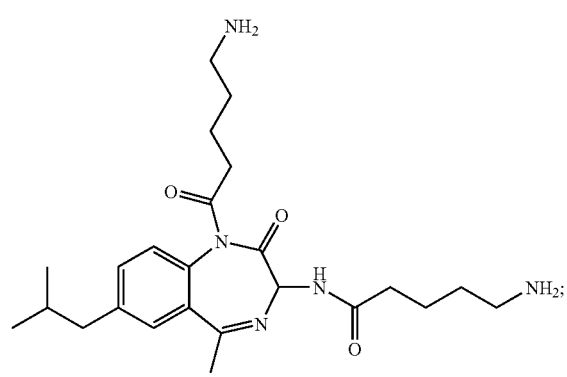
5
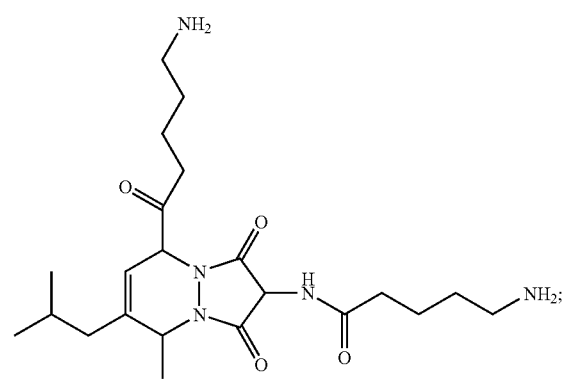
6
-continued
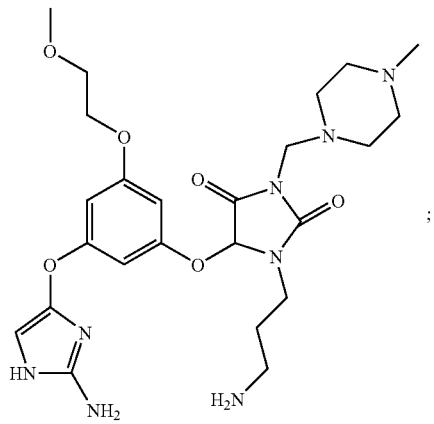
7
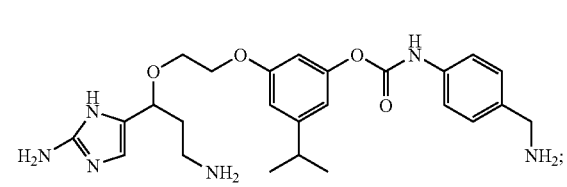
8
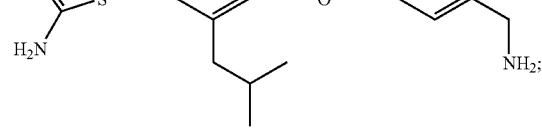
9
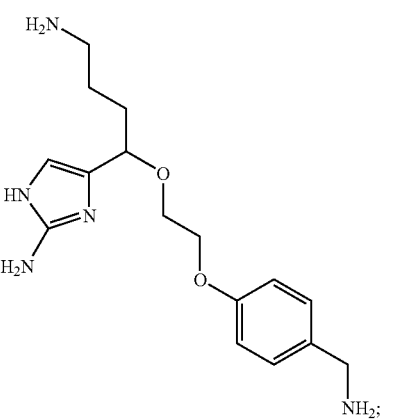
10
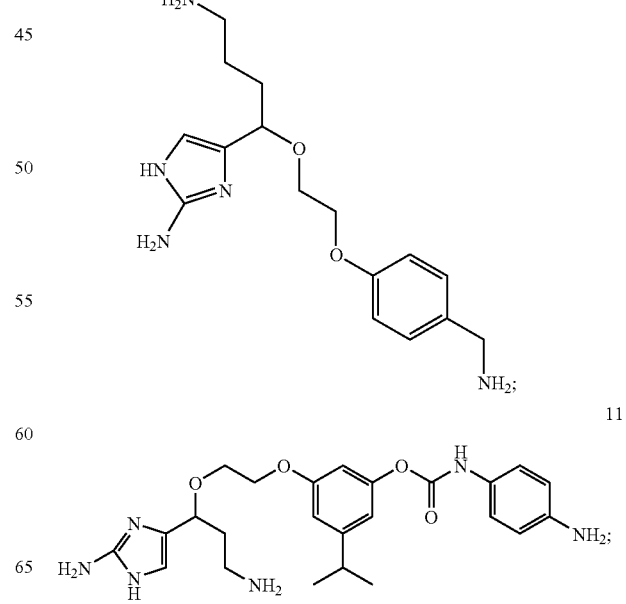
11

-continued

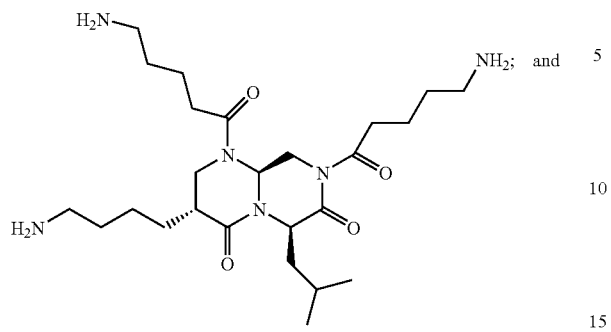

12

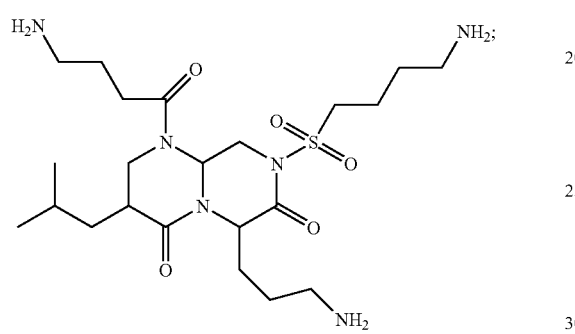

13

(b) a pharmaceutically acceptable salt of the compound of (a);

(c) the compound of any of (b), further comprising a heterologous polypeptide or peptide or a non-protein moiety;

(d) the compound of (c), wherein the compound, and/or the polypeptide or peptide, is conjugated to a carrier;

(e) the compound of (d), wherein the carrier comprises or consists of a poly-Arg, a TAT or a *Drosophila antennapedia* homeodomain; or (f) the compound of any of (a) to (e), further comprising at least one pharmaceutically acceptable excipient.

The invention provides compounds comprising or consisting of:

(a) formula selected from the group consisting of

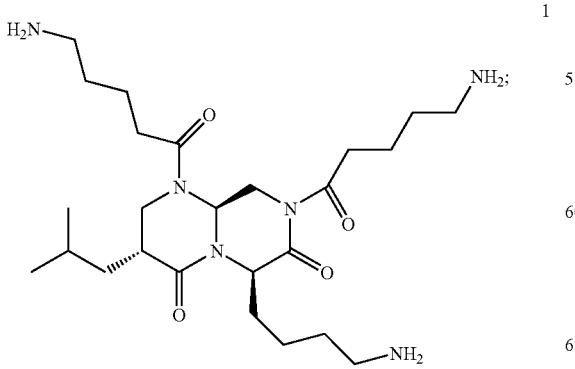

1

-continued

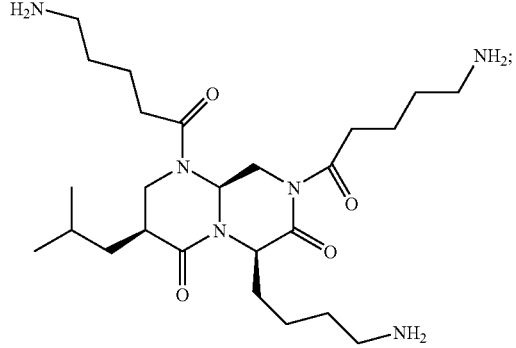

2

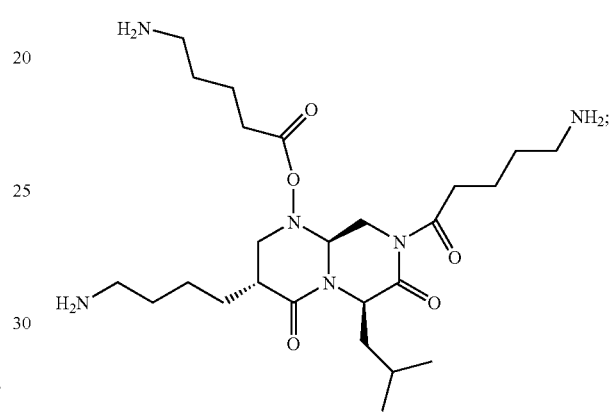

3

4

5

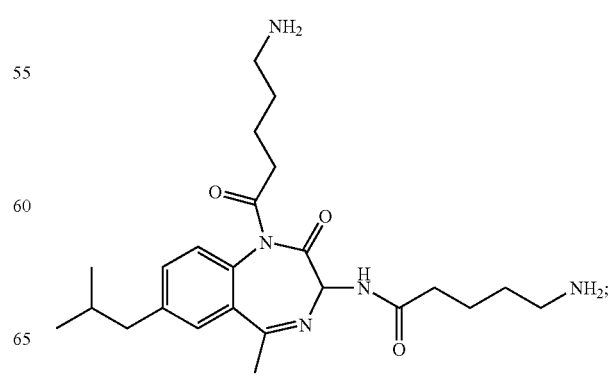

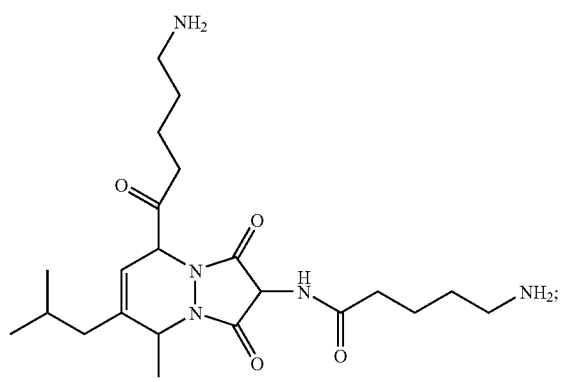

6

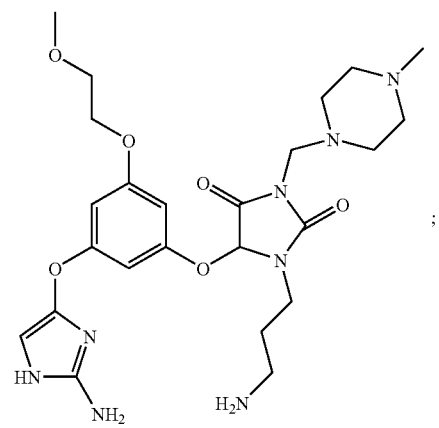

7

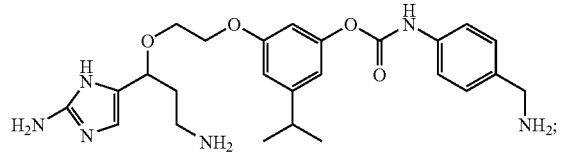

8

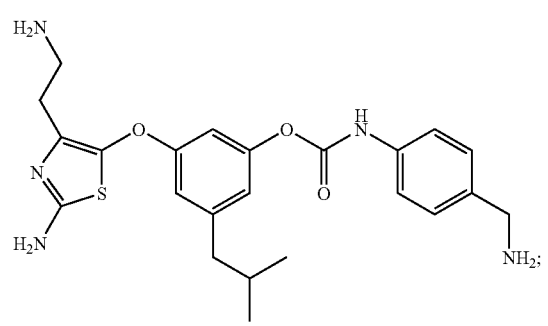

9

10

11

12

13

(b) a pharmaceutically acceptable salt of the compound of (a);
(c) the compound of any of (b), further comprising a heterologous polypeptide or peptide or a non-protein moiety;
(d) the compound of (c), wherein the compound, and/or the polypeptide or peptide, is conjugated to a carrier;
(e) the compound of (d), wherein the carrier comprises or consists of a poly-Arg, a TAT or a *Drosophila antennapedia* homeodomain; or
(f) the compound of any of (a) to (e), further comprising at least one pharmaceutically acceptable excipient.

The invention provides pharmaceutical compositions comprising at least one polypeptide or peptide of the invention, and/or at least one compound of the invention, and at least one pharmaceutically acceptable excipient.

The invention provides pharmaceutical formulations comprising:
(a) at least one polypeptide or peptide of the invention, and/or at least one compound of the invention; or
(b) the pharmaceutical formulation of (a), formulated as an aqueous suspension, a solid, a liquid, a powder, an emulsion, a lyophilized powder, a spray, a cream, a lotion, a controlled release formulation, a tablet, a pill, a gel, a liposome, on a patch, in an implant, on a tape, a dragee, a capsule, a lozenge, a gel, a syrup, a slurry and/or a suspension.

The invention provides liposomes comprising at least one polypeptide or peptide of the invention, and/or at least one compound of the invention, and/or at least one pharmaceutical composition of the invention, and/or at least one pharmaceutical formulation of the invention.

The invention provides nanoparticles comprising at least one polypeptide or peptide of the invention, and/or at least one compound of the invention, and/or at least one pharmaceutical composition of the invention, and/or at least one pharmaceutical formulation of the invention.

The invention provides uses of one polypeptide or peptide of the invention, and/or at least one compound of the invention, for the manufacture of a medicament.

The invention provides uses of one polypeptide or peptide of the invention, and/or at least one compound of the invention, for the manufacture of a medicament for (a) the treatment, prevention or amelioration of diseases or conditions associated with a protein aggregation; (b) preventing, reversing, slowing or inhibiting synuclein, beta-amyloid and/or tau protein aggregation; or (c) preventing, reversing, slowing or inhibiting a neurodegenerative disease associated with protein aggregation.

The invention provides use of at least one polypeptide or peptide of the invention, and/or at least one compound of the invention, for the manufacture of a medicament for the treatment, prevention or amelioration of Parkinson's disease (PD), Alzheimer's Disease (AD), Lewy body disease (LBD) or Multiple system atrophy (MSA).

The invention provides methods for the treatment, prevention or amelioration of a disease or a condition associated with protein aggregation in an individual comprising administration of an effective amount of at least one polypeptide or peptide of the invention, and/or at least one compound of the invention, and/or at least one pharmaceutical composition of the invention, and/or at least one pharmaceutical formulation of the invention, and/or at least one liposome of the invention, and/or at least one nanoparticle of the invention.

In one embodiment of the methods of this invention, the method comprises (a) reversing, slowing or inhibiting synuclein, beta-amyloid and/or tau protein aggregation; or (b) preventing, reversing, slowing or inhibiting a neurodegenerative disease associated with protein aggregation. In one embodiment of the methods of this invention, the disease or condition associated with protein aggregation is Parkinson's disease (PD), Alzheimer's Disease (AD), Lewy body disease (LBD) and/or Multiple system atrophy (MSA).

The invention provides methods for preventing, inhibiting, reversing or slowing aggregation of a polypeptide or peptide, comprising contacting a cell with at least one polypeptide or peptide of the invention, and/or at least one compound of the invention, and/or at least one pharmaceutical composition of the invention, and/or at least one pharmaceutical formulation of the invention, and/or at least one liposome of the invention, and/or at least one nanoparticle of the invention.

The invention provides methods for preventing, inhibiting, reversing or slowing a neurodegenerative process, a disease or a condition to an individual in need thereof, comprising
(a) administering to the individual at least one polypeptide or peptide of the invention, and/or at least one compound of the invention, and/or at least one pharmaceutical composition of the invention, and/or at least one pharmaceutical formulation of the invention, and/or at least one liposome of the invention, and/or at least one nanoparticle of the invention;
(b) the method of (a), wherein the administration comprises contacting a nerve cell with at least one polypeptide or peptide of the invention, and/or at least one compound of the invention, and/or at least one pharmaceutical composition of the invention, and/or at least one pharmaceutical formulation of the invention, and/or at least one liposome of the invention, and/or at least one nanoparticle of the invention; or
(c) the method of (a) or (b), wherein the contacting is in vitro, ex vivo or in vivo.

The invention provides methods for interfering in the accumulation of protein or peptide aggregation in a cell, or reversing protein or peptide aggregation in a cell, or preventing protein or peptide aggregation in a cell, comprising:
(a) contacting the cell with an effective amount of at least one polypeptide or peptide of the invention, and/or at least one compound of the invention, and/or at least one pharmaceutical composition of the invention, and/or at least one pharmaceutical formulation of the invention, and/or at least one liposome of the invention, and/or at least one nanoparticle of the invention; or
(b) the method of (a), wherein the contacting is in vitro, ex vivo or in vivo.

The invention provides kits comprising at least one polypeptide or peptide of the invention, and/or at least one compound of the invention, and/or at least one pharmaceutical composition of the invention, and/or at least one pharmaceutical formulation of the invention, and/or at least one liposome of the invention, and/or at least one nanoparticle of the invention, and instructions comprising use of any one or more methods of the invention.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

DESCRIPTION OF DRAWINGS

FIG. 1 illustrates specific inter-molecular interactions between two head-to-head α-syn monomers over time (4 ns), and demonstrates the critical sites of interaction (rectangles) toward the formation of propagating dimer. In the sequence illustration of α-syn in the upper panel, membrane-contacting N-terminal (n-term) regions are designated by boxes and C-terminal (c-term) regions by lines, as viewed perpendicular to the membrane surface. In the lower panels, various dockings are illustrated: for example, the second α-syn molecule (α-syn 2) docks to the first (α-syn 1), followed by docking of the third α-syn molecule (α-syn 3) to the second, etc., considering minimal docking energies from all possible docking positions. FIG. 1 bottom panel illustrates a non-propagating conformation (head-to-tail) of two α-syn monomers that prevents low-energy docking of additional monomers. FIG. 1 bottom panel illustrates a propagating conformation that allows low energy docking of additional monomers added sequentially (in the direction of the arrow).

FIG. 2A, left panel illustration, illustrates the final configuration of the hexamer after 3.5 ns on the membrane, as a side view. FIG. 2B, middle panel illustration, illustrates the modeling of multimers at various time points between 1.5 and 4.5 ns, as a top view. The table to the right margin (right-handed panel) indicates the inner diameters (ID) and outer diameters (OD) of the multimers created from the conformers obtained at the various molecular dynamics (MD) time points.

FIG. 3A illustrates an immunoblot demonstrating in vitro cell-free aggregation of α-syn monomers into dimers, trimers, tetramers, pentamers and hexamers over time. FIG. 3B graphically illustrates data of a semi-quantitative analysis demonstrating levels of α-syn multimers formed over time. FIG. 3C, FIG. 3D, FIG. 3E and FIG. 3F: illustrate electron microscopy analysis of α-syn aggregation over time into ring-like structures and fibrils; the electron microscopy analyses of FIG. 3C, FIG. 3D, FIG. 3E and FIG. 3F demonstrate a reduction in α-syn aggregation over time; in FIG. 3F bar=20 nm. FIG. 3G illustrates superimposition of α-syn pentamer (4.5 ns) onto the ring-like structure detected by electron microscopy; bar=10 nm. Figure H illustrates modeling of the embedded α-syn complex in the membrane over time: this is a top view, at the level of the uppermost membrane-associated atom, of the embedded portion of the α-syn pentamer (350 ps) on the POPC membrane; white=α-syn pentamer; green=membrane phospholipids.

FIG. 3I and FIG. 3J are micrograph illustrations of HEK293T cells, showing that cells transduced with lentiviral vectors encoding α-syn and GFP express comparable protein levels. FIG. 3K, FIG. 3L and FIG. 3M graphically illustrate data showing representative currents elicited by depolarizing the cells from a holding potential of −50 mv to a series of test potentials ranging from −80 to +80 mv, and corresponding current-voltage relationship (E; means±SE) in transduced cells. Cells expressing α-syn display a significant increase in ion currents. FIG. 3N left panel graphically illustrates representative currents at +80 mv (left panel) before (Cont), during ($Zn^{2+}$) and after (Wash) application of 500 µM $Zn^{2+}$. FIG. 3N, right panel, graphically illustrates the time course of the change in current density before, during, and after extracellular application of $Zn^{2+}$. The arrows correspond to the currents shown in the left panel (Cont, a; $Zn^{2+}$, b; and Washout, c). The increased currents in cells expressing α-syn are attenuated by $Zn^{2+}$.

FIG. 5A illustrates a representation with side chains of the exemplary KKDQLGK (SEQ ID NO:1) peptide of the invention docking to the c-terminus of α-syn. FIG. 5B illustrates that a docked peptide of this invention blocks dimer formation.

FIG. 6A illustrates a representation of peptidomimetic compound of this invention docking to the c-terminus of α-syn. FIG. 6B illustrates that a docked peptidomimetic compound of this invention blocks dimer formation.

FIG. 7A and FIG. 7B illustrate cell free immunoblot assays showing reduced aggregation at 37° C. and 65° C. using the exemplary peptide of this invention (96-102) KKDQLGK peptide, (SEQ ID NO:1); and FIG. 7C graphically summarizes this data. FIG. 7D and FIG. 7E are photomicrograph illustrations demonstrating that neuronal cultures overexpressing α-syn showed reduced accumulation of α-syn dimer upon treatment with the exemplary KKDQLGK peptide of this invention (SEQ ID NO:1) at 1 uM.

FIG. 8 illustrates a pyrimido-pyrazine exemplary scaffold, a pyridazine-dione exemplary scaffold, and a benzodiazepine exemplary scaffold, where R1, R2, R4 are basic amino acid residues, and R3 is an aliphatic short chain hydrocarbon, as discussed in detail the Examples, below.

FIG. 13B illustrates the docking of a variation of the exemplary peptidomimetic of this invention illustrated in FIG. 11, into the binding pocket of alpha-synuclein; in this structure the R2 and R 3 positions of the structure illustrated in FIG. 11 were switched, as discussed in detail the Examples, below.

FIG. 18A is a micrograph illustration showing that in neuronal cultures overexpressing α-syn there is a significant time dependent increase in intracellular calcium influx as determined by Fluo-4 and the FLIPR assay. FIG. 18B is a micrograph illustration of the neuronal cultures after treatment with the exemplary 96-102 KKDQLGK (SEQ ID NO:1) peptide of this invention, where the cultures have reduced neuronal calcium influx after 24 hrs at 37° C. (arrow) compared to vehicle and scrambled peptide controls. Data from these studies is graphically summarized on the right hand panels.

FIG. 19A illustrates the experimental design: for these studies the thy1-overexpressing α-syn received intraventricular infusions with osmotic minipumps of control scrambled peptide, or the exemplary peptide of this invention 96-102 KKDQLGK (SEQ ID NO:1) for 6 weeks, at 30 µM peptide, where 200 µl of solution is minipumped into the lateral ventricle of the animal. FIG. 19B is a micrograph illustrating that infusion of the exemplary peptide of this invention, the 96-102 KKDQLGK (SEQ ID NO:1) peptide, resulted in a significant reduction in neuronal α-syn accumulation in the hippocampus, as compared to scrambled peptide controls; and FIG. 19C graphically summarizes this data (where "blocker" is the 96-102 KKDQLGK (SEQ ID NO:1) peptide).

DETAILED DESCRIPTION

Figure 1:
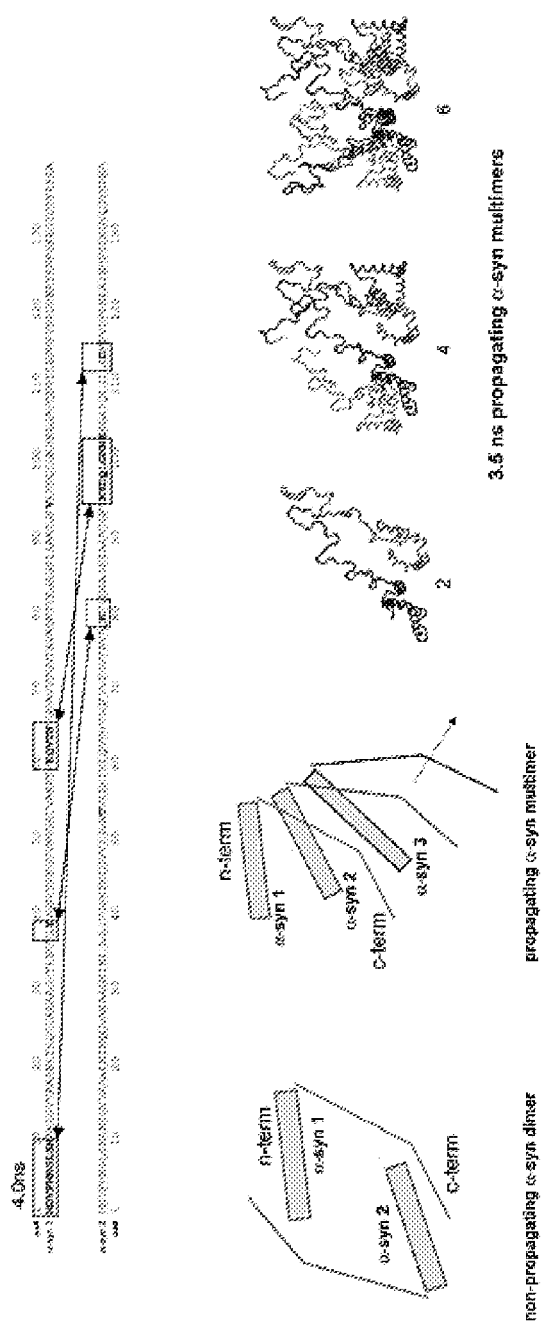
FIG. 1 illustrates molecular dynamics studies of the critical sites in the α-syn dimers that mediate aggregation leading to oligomer formation, as discussed in detail the Examples, below.

The invention provides a novel approach to the treatment of degenerative neurological diseases that are characterized by protein aggregation. In alternative embodiments, the compositions and methods of the invention are used to specifically target synuclein, amyloid and/or tau aggregates, and the approach is potentially applicable to other protein aggregates. In alternative embodiments, the compositions and methods of the invention are used to slow, prevent or stop protein aggregation and/or to mitigate deleterious effects that are secondary to the protein aggregation, but also contribute to neuronal death.

In alternative aspects, the compositions and methods of the invention are used to specifically target synuclein aggregation; and while the invention is not limited by any particular mechanism of action, synuclein aggregation is thought to be caused by a mis-alignment of the protein early in the disease process, which permits the formation of protein multimers due to head-to-head aggregation; as the monomer units increase, the aggregated proteins can take on a pore-like shape, which can embed in the membrane of the neuron, disrupting ion flow and homeostasis of the cell.

In alternative aspects, the compositions and methods of the invention comprise use of peptides to block, reverse or inhibit synuclein aggregation or 'seal' the pore-like structure, thus preventing additional or increased protein aggregation and/or repair the disruption in the ion flux. Using these peptides of the invention as guides as guides, the inventors have utilized structure based design tools to design two small 'core' molecules that have the same effect as the peptides; these molecules appear to be novel, require no covalent interaction with the aggregate but rely on hydrogen bonding, polar and hydrophobic interactions and have no obvious constituents that are problematic metabolically.

The invention also provides methods for testing the efficacy of compositions, including small molecules and/or peptides, to block, reverse or inhibit protein, e.g., synuclein, aggregation in an in-vitro (cell free) system and in a neuronal cell line; assays have been conducted for aggregation, growth and survival of cells. The small molecules and/or peptides can be tested in Syn Tg mice.

Upon interactions with lipids in the membrane, SYN can adopt a conformation that under pathological conditions can result in the formation neurotoxic SYN aggregates. A specific section within the c-terminal region of SYN mediates this aggregation effect. The invention takes advantage of this region and describes a series of peptides (e.g., amino acids 96-102 of human SYN, (SEQ ID NO:1) KKDQLGK) and examples of peptidomimetic tricyclical compound [3-(2-amino-4-(2-aminoethyl)thiazol-5-yloxy)-5-isobutylphenyl 4-(aminomethyl)phenylcarbamate] and bicyclical compounds derived from structure based design that block SYN aggregation and neurodegeneration in an in vitro model system. Thus, compounds of this invention can be used as therapy for PD, LBD, AD and MSA, and while the invention is not limited by any particular mechanism of action, compounds of this invention can be used to block neurotoxic SYN oligomerization in the cell membrane.

The invention provides a model comprising use of the abnormally aggregated SYN to identify sites in the molecule that facilitate oligomerization and designed peptides that might block further aggregation. From the peptides tested in vitro we selected a sequence that was most effective at blocking specifically SYN aggregation. Then a series of peptidomimetic compounds were generated using structure-based design. The tricyclic and bicyclic compounds were specifically designed to recognize a portion in the c-terminal region of abnormal SYN and block further aggregation. Such base compounds and a series of derivatives have not been previously described as inhibitors of SYN aggregation and represent a completely new avenue for treatment development for PD and related disorders. This invention for the first time describes specific peptidomimetic compounds for blocking SYN aggregation.

Chemical Definitions

In one aspect, "alkenyl" and "alkynyl" groups are defined similarly to alkyl groups, and include straight-chain, branched-chain and cyclic monovalent hydrocarbyl radicals, and combinations of these, which contain only C and H when they are unsubstituted. In alternative embodiments, alkenyl groups contain one or more carbon-carbon double bonds, and/or alkynyl groups contain one or more carbon-carbon triple bonds.

In alternative embodiments, the alkyl, alkenyl and alkynyl substituents of the invention contain 1-8C (alkyl) or 2-8C (alkenyl or alkynyl). In alternative aspects, they contain 1-4C (alkyl) or 2-4C (alkenyl or alkynyl).

In alternative embodiments, alkyl, alkenyl and alkynyl groups are substituted to the extent that such substitution makes sense chemically. In alternative aspects, substituents include, but are not limited to, halo, =O, —CN, —OR', —SR', —S(O)R', —SO$_2$R', —COOR', —C(O)NR'$_2$, —NR'$_2$ and —NHC(=NH)NH$_2$, where each R' independently represents H, C1-C4 alkyl or C5-C12 arylalkyl, or a heteroform of one of these.

In alternative embodiments, "Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain one or more heteroatoms selected from O, S and N and combinations thereof, within the backbone residue. When heteroatoms (in alternative embodiments can be N, O and S) are allowed to replace carbon atoms of an alkyl, alkenyl or alkynyl group, as in heteroalkyl groups, the numbers describing the group, though still written as e.g. C1-C6, represent the sum of the number of carbon atoms in the group plus the number of such heteroatoms that are included as replacements for carbon atoms in the ring or chain being described. Such heteroalkyl groups may be optionally substituted with the same substituents as alkyl groups.

Where such groups contain N, the nitrogen atom may be present as NH or it may be substituted if the heteroalkyl or similar group is described as optionally substituted. Where such groups contain S, the sulfur atom may optionally be oxidized to SO or SO$_2$ unless otherwise indicated. For reasons of chemical stability, it is also understood that, unless otherwise specified, such groups do not include more than two contiguous heteroatoms as part of the heteroalkyl chain, although an oxo group may be present on N or S as in a nitro or sulfonyl group. Thus —C(O)NH$_2$ can be a C2 heteroalkyl group substituted with =O; and —SO$_2$NH— can be a C2 heteroalkylene, where S replaces one carbon, N replaces one carbon, and S is substituted with two =O groups.

While "alkyl" in one aspect includes cycloalkyl and cycloalkylalkyl groups, the term "cycloalkyl" may be used herein to specifically describe a carbocyclic non-aromatic group that is connected via a ring carbon atom, and "cycloalkylalkyl" may be used to describe a carbocyclic non-aromatic group that is connected to the base molecule through an alkyl linker. For example, cyclohexylalanine (Cha) comprises a cycloalkylalkyl substituent. Similarly, "heterocyclyl" may be used to describe a non-aromatic cyclic group that contains at least one heteroatom as a ring member and that is connected to the molecule via a ring atom of the cyclic group, which may be C or N; and "heterocyclylalkyl" may be used to describe such a group that is connected to another molecule through an alkyl linker. The sizes and substituents that are suitable for the cycloalkyl, cycloalkylalkyl, heterocyclyl, and heterocyclylalkyl groups are the same as those described above for alkyl groups. Where an alkyl group is substituted with an aryl or heteroaryl group, it is referred to as an arylalkyl or heteroarylalkyl substituent.

In one aspect, an "aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, pyridazinyl, triazinyl, thienyl, furanyl, pyrrolyl, pyrazolyl, thiazolyl, isothiazolyl, oxazolyl, isoxazolyl, imidazolyl, triazolyl, thiadiazolyl, oxadiazolyl, and tetrazolyl rings, and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolinyl, quinolinyl, benzothiazolyl, benzofuranyl, benzothienyl, benzisoxazolyl, pyrazolopyridyl, quinazolinyl, quinoxalinyl, cinnolinyl, and the like.

Any monocyclic or fused ring bicyclic system which has the characteristics of aromaticity in terms of electron distribution throughout the ring system is included in this definition. It also includes bicyclic groups where at least one ring has the characteristics of aromaticity, even though it may be fused to a nonaromatic ring. In alternative embodiments, the ring systems contain 5-12 ring member atoms. In alternative aspects, the monocyclic heteroaryl groups contain 5-6 ring members, and the bicyclic heteroaryls contain 8-10 ring members.

Aryl and heteroaryl moieties may be substituted with a variety of substituents which are known in the art. In alternative aspects, substituents include, but are not limited to, halo, C1-C8 alkyl, —NO$_2$, —CN, —OR', —SR', —COOR', —C(O)NR'$_2$, and —NR'$_2$, where each R' independently represents H, C1-C4 alkyl or C5-C12 arylalkyl, or a heteroform of one of these.

In alternative embodiments, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. In alternative embodiments, the linker is C1-C8 alkyl or a hetero form thereof. These linkers may also include a carbonyl group, thus making them able to provide substituents as an acyl or heteroacyl moieties. "Heteroarylalkyl" refers to a moiety comprising an aryl group that is attached through a linking group, and differs from "arylalkyl" in that at least one ring atom of the aryl moiety or one atom in the linking group is a heteroatom selected from N, O and S.

An aryl or heteroaryl ring in an arylalkyl or heteroarylalkyl group may be optionally substituted on the aromatic portion with the same substituents described above for aryl groups. In alternative embodiments, an arylalkyl group includes a phenyl ring and a heteroarylalkyl group includes a C5-C6 monocyclic or C8-C10 fused bicyclic heteroaromatic ring, each of which may be optionally substituted with the groups defined above for aryl groups and a C1-C4 alkylene that is unsubstituted or is substituted with one or two C1-C4 alkyl groups, where the alkyl groups can optionally cyclize to form a ring, and wherein the alkyl or heteroalkyl groups may be optionally fluorinated. In certain embodiments, the arylalkyl or heteroarylalkyl ring comprises a phenol or an indole ring. In alternative aspects, substituents on phenyl include OH, C1-C4 alkoxy, and halo.

"Arylalkyl" and "heteroarylalkyl" groups are described by the total number of carbon atoms in the ring and alkylene or similar linker. In alternative embodiments, a benzyl group is a C7-arylalkyl group, and phenethyl is a C8-arylalkyl group.

"Alkylene" in one aspect refers to a divalent hydrocarbyl group; because it is divalent, it can link two other groups together. In alternative embodiments, it refers to —$(CH_2)_n$— where n is 1-8, or n is 1-4, though where specified, an alkylene can also be substituted by other groups, and can be of other lengths, and the open valences need not be at opposite ends of a chain. In alternative embodiments, —CH(Me)— and —$C(Me)_2$- are referred to as alkylenes, as can a cyclic group such as cyclopropan-1,1-diyl. In alternative embodiments, for clarity, a three-atom linker that is an alkylene group, for example, refers to a divalent group in which the available valences for attachment to other groups are separated by three atoms such as —$(CH_2)_3$—, i.e., the specified length represents the number of atoms linking the attachment points rather than the total number of atoms in the hydrocarbyl group: —$C(Me)_2$- would thus be a one-atom linker, since the available valences are separated by only one atom. In alternative embodiments, where an alkylene group is substituted, the substituents include those present on alkyl groups, e.g., as described herein, thus —C(=O)— is an example of a one-carbon substituted alkylene. In alternative embodiments, where it is described as unsaturated, the alkylene may contain one or more double or triple bonds.

"Heteroalkylene" in one aspect is defined similarly to the corresponding alkylene groups, but the 'hetero' terms refer to groups that contain one or more heteroatoms selected from O, S and N and combinations thereof, within the backbone residue; thus at least one carbon atom of a corresponding alkylene group is replaced by one of the specified heteroatoms to form a heteroalkylene group. In alternative embodiments, —C(=O)NH— is an example of a two-carbon substituted heteroalkylene, where N replaces one carbon, and C is substituted with a =O group.

Figure 8:
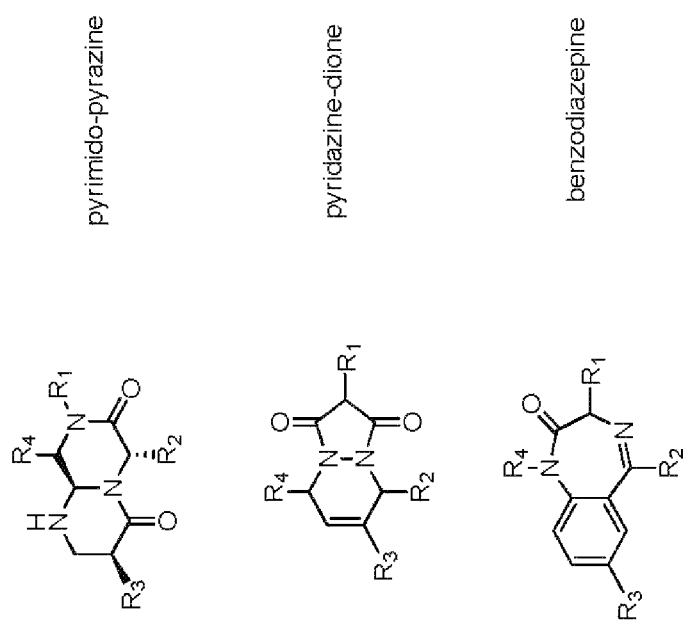
FIG. 8 illustrates three exemplary bicyclic peptidomimetics of this invention that can be made from different exemplary scaffolds of this invention; these peptido-scaffolds can be used to synthesize alpha-synuclein inhibitors of this invention, as discussed in detail the Examples, below.
Figure 9:
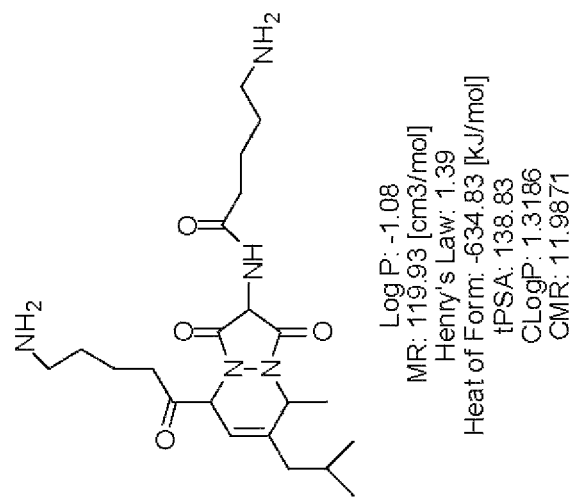
FIG. 9 illustrates an exemplary peptidomimetic of this invention that can be synthesized from the pyrazidine-dione scaffold of FIG. 8; the figures also lists some predicted basic drugability parameters for this compound, as discussed in detail the Examples, below.
Figure 10:
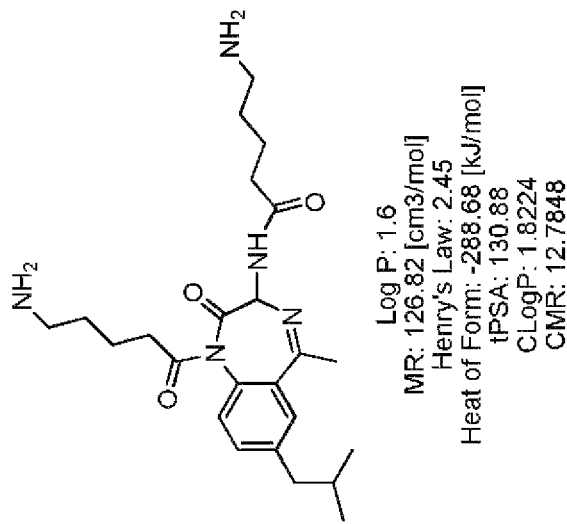
FIG. 10 illustrates an exemplary peptidomimetic of this invention that can be synthesized from the benzodiazepine scaffold of FIG. 8; the figures also lists some predicted basic drugability parameters for this compound, as discussed in detail the Examples, below.
Figure 11:
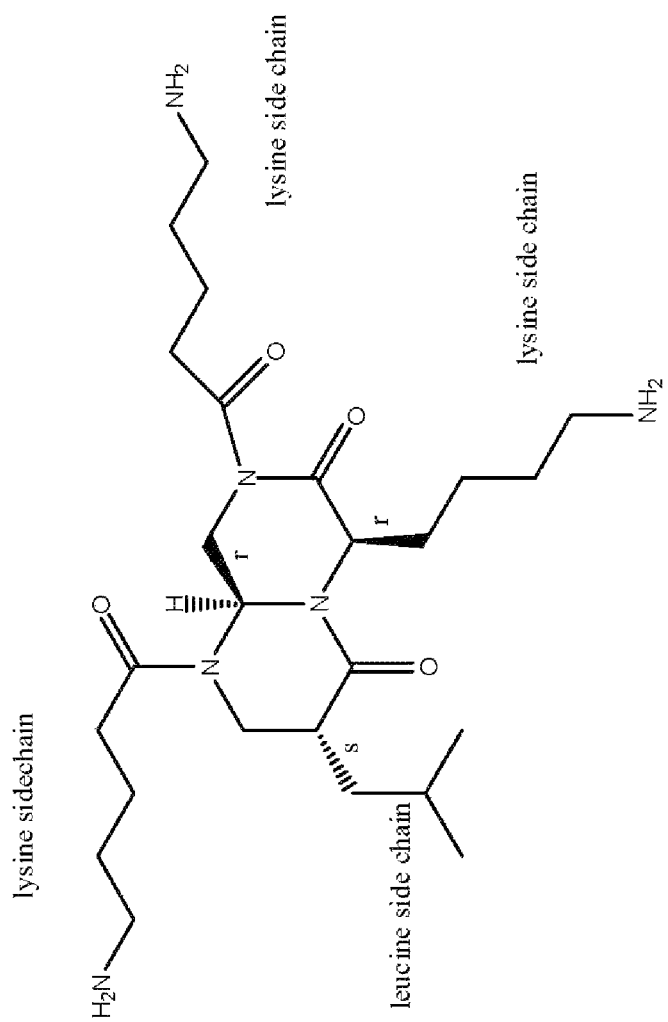
FIG. 11 illustrates an exemplary peptidomimetic of this invention that can be synthesized from the pyrimido-pyrazine scaffold of FIG. 8, as discussed in detail the Examples, below.

In one aspect, an "aminoalkyl" group refers to a C1-C6 alkyl group that is substituted with at least one amine group having the formula —NR2, where each $R_1$, $R_2$, $R_3$ and/or $R_4$ group (see FIG. 8) is independently H, C1-C8 alkyl, C5-C12 aryl and C5-C12 arylalkyl, or a heteroform of one of these. Such aminoalkyl groups may be optionally substituted on the alkyl portion with one or more other groups suitable as substituents for an alkyl group. In some embodiments, the aminoalkyl substituent is a 1-aminoalkyl group such as a 1-aminomethyl, 1-aminoethyl, 1-aminopropyl or 1-aminobutyl group. In certain embodiments, the aminoalkyl group may comprise a protected amine. One of skill in the art would appreciate that appropriate amine protecting groups may vary depending on the functionality present in the particular monomer. Suitably protected amines may include, for example, carbamates (e.g. tert-butoxycarbonyl, benzyloxycarbonyl, fluorenylmethyloxy-carbonyl, allyloxycarbonyl or (trialkylsilyl)ethoxycarbonyl), carboxamides (e.g. formyl, acyl or trifluoroacetyl), sulfonamides, phthalimides, Schiff base derivatives, and the like. In certain embodiments, an aminoalkyl group may be coupled through an alkylene or heteroalkylene linker to a group such as biotin, or a fluorophore-containing group, such as rhodamine, and such compounds may be useful for screening or mechanistic studies.

"Heteroform" in one aspect refers to a derivative of a group such as an alkyl, aryl, or acyl, wherein at least one carbon atom of the designated carbocyclic group has been replaced by a heteroatom selected from N, O and S. In alternative embodiments, the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. In alternative embodiments, no more than two N, O or S atoms are ordinarily connected sequentially, except where an oxo group is attached to N or S to form a nitro or sulfonyl group.

"Optionally substituted" in one aspect indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

"Halo", in one aspect includes fluoro, chloro, bromo and iodo. Fluoro and chloro can be used.

"Amino" in one aspect refers to an $NR'_x$ wherein $R'_x$ can be independently H, or is an alkyl, alkenyl, alkynyl, acyl, aryl, or arylalkyl group or a heteroform of one of these groups, as defined above, each of which may be optionally substituted with the substituents described herein as suitable for the corresponding type of group. In certain embodiments, the two R' groups on one nitrogen atom may be linked together to form an azacyclic ring.

In one aspect, an 'azacyclic' group refers to a heterocyclic group containing at least one nitrogen atom as a ring atom, wherein the group is attached to the base molecule through a nitrogen atom of the azacyclic group. In alternative embodiments, azacyclic groups are 3-8 membered monocyclic rings or 8-12 membered bicyclic fused ring systems, and may be saturated, unsaturated or aromatic and may contain a total of 1-3 heteroatoms independently selected from N, O and S as ring members. In certain embodiments, an azacyclic ring may comprise a nitrogen-containing ring fused to a phenyl ring. For example, the unnatural amino acid "Tic" comprises a tetrahydroisoquinoline ring, which represents a 10-membered fused bicyclic azacyclic group.

The invention provides nanoparticles comprising any compound of this invention, or a compound made by any of the biosynthetic or synthetic methods of this invention.

Figure 12:
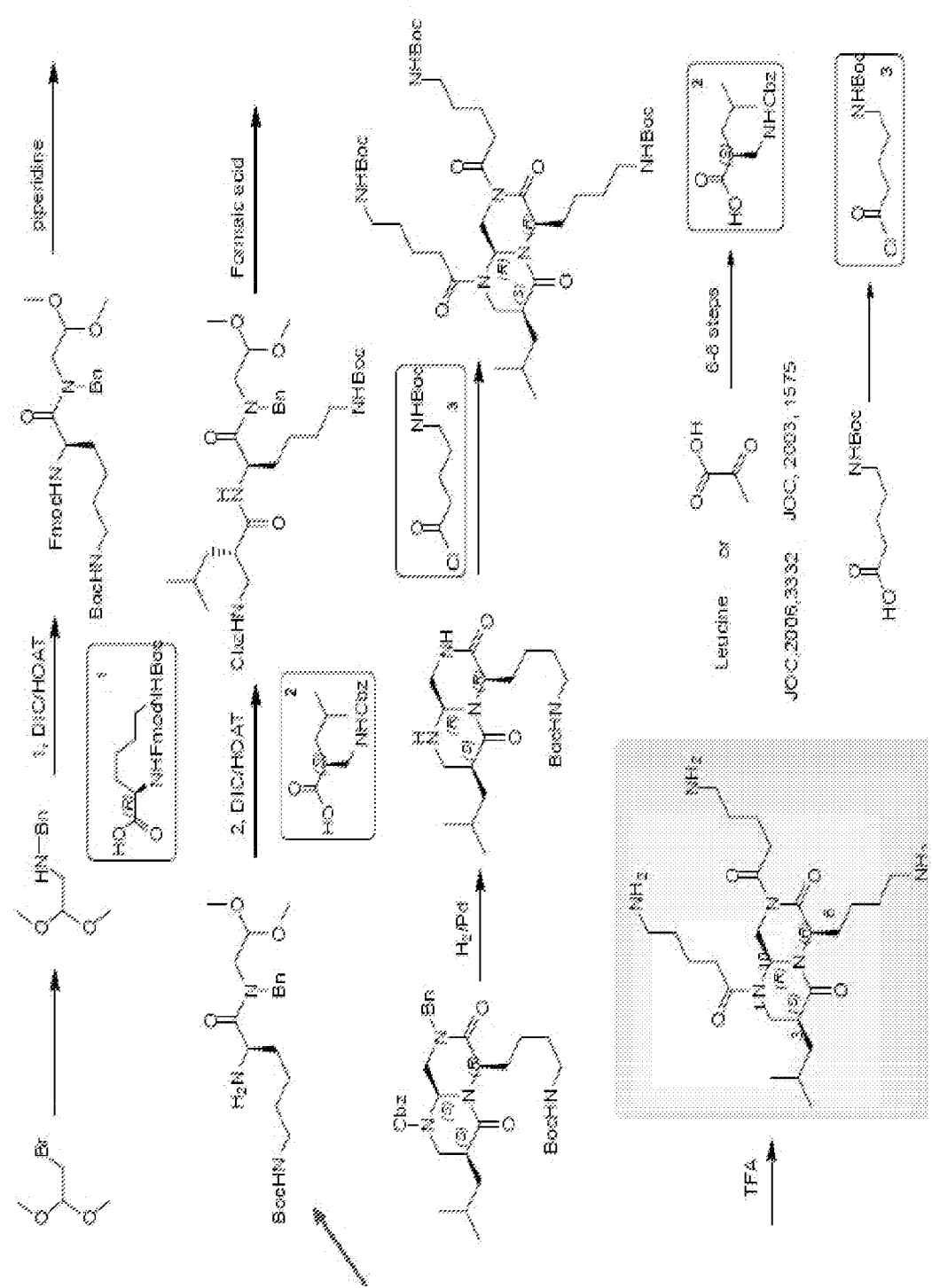
FIG. 12 illustrates an exemplary synthetic scheme of this invention for the exemplary peptidomimetic of this invention illustrated in FIG. 11, as discussed in detail the Examples, below.
Figure 13A:
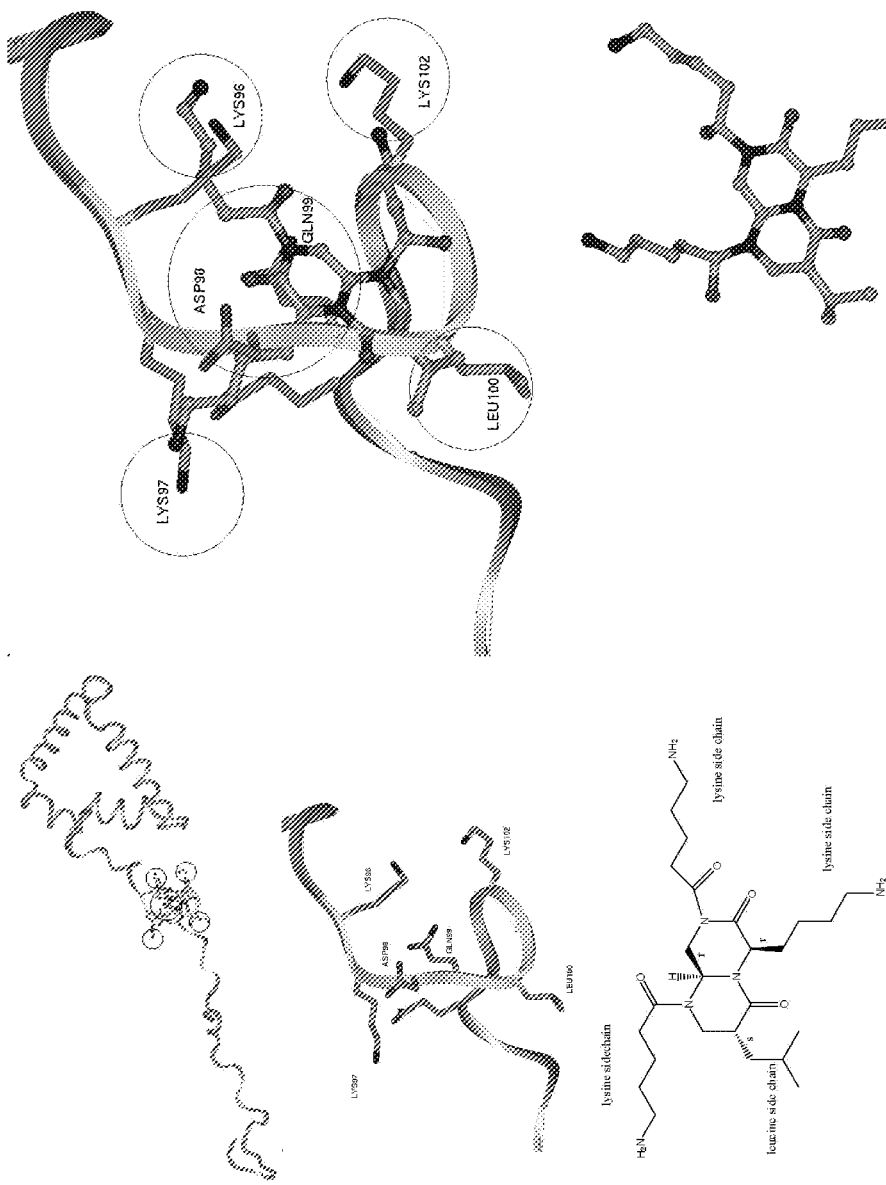
FIG. 13A illustrates the docking of the structure of the prototype compound shown in FIG. 11 into the binding region of alpha-synuclein, as discussed in detail the Examples, below.
Figure 14:
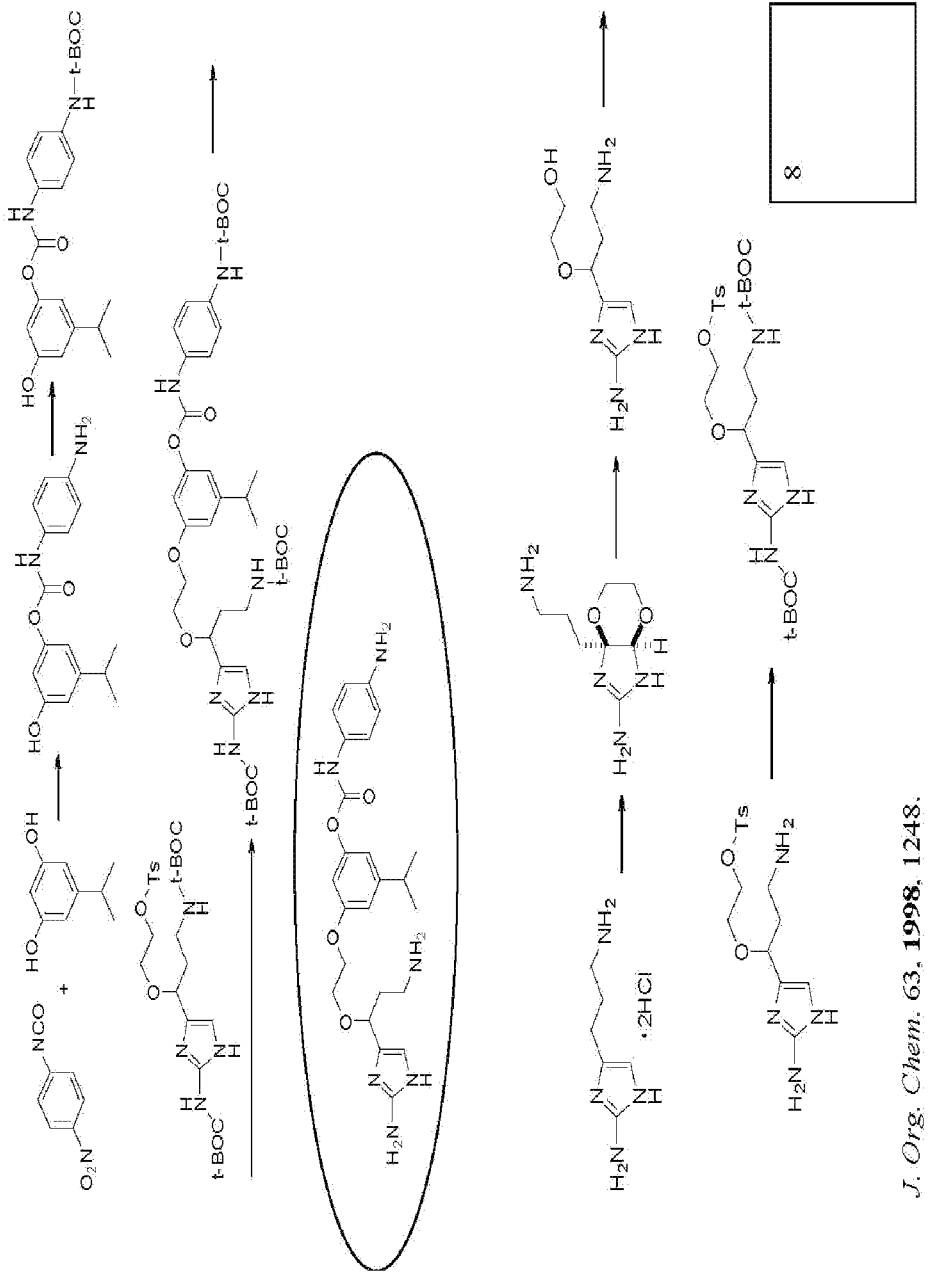
FIG. 14 illustrates an exemplary synthetic scheme of this invention: a synthetic scheme for the synthesis of the exemplary peptidomimetic of this invention illustrated in FIG. 11: an exemplary inhibitor of alpha-synuclein based on a benzo-ether scaffold in place of the peptidomimetic scaffolds of this invention as illustrated in FIG. 8, as discussed in detail the Examples, below.
Figure 15:
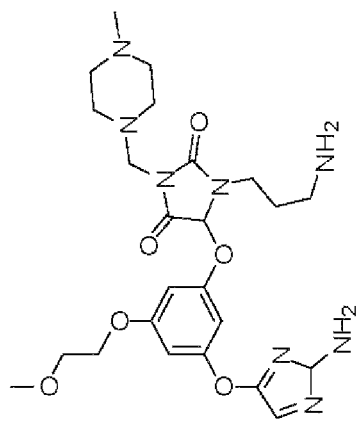
FIG. 15 illustrates an exemplary inhibitor of this invention of the benzoether type with at least one heterocyclic moiety (one or more heterocyclic moieties) for diversity inputs, as discussed in detail the Examples, below.
Figure 16:
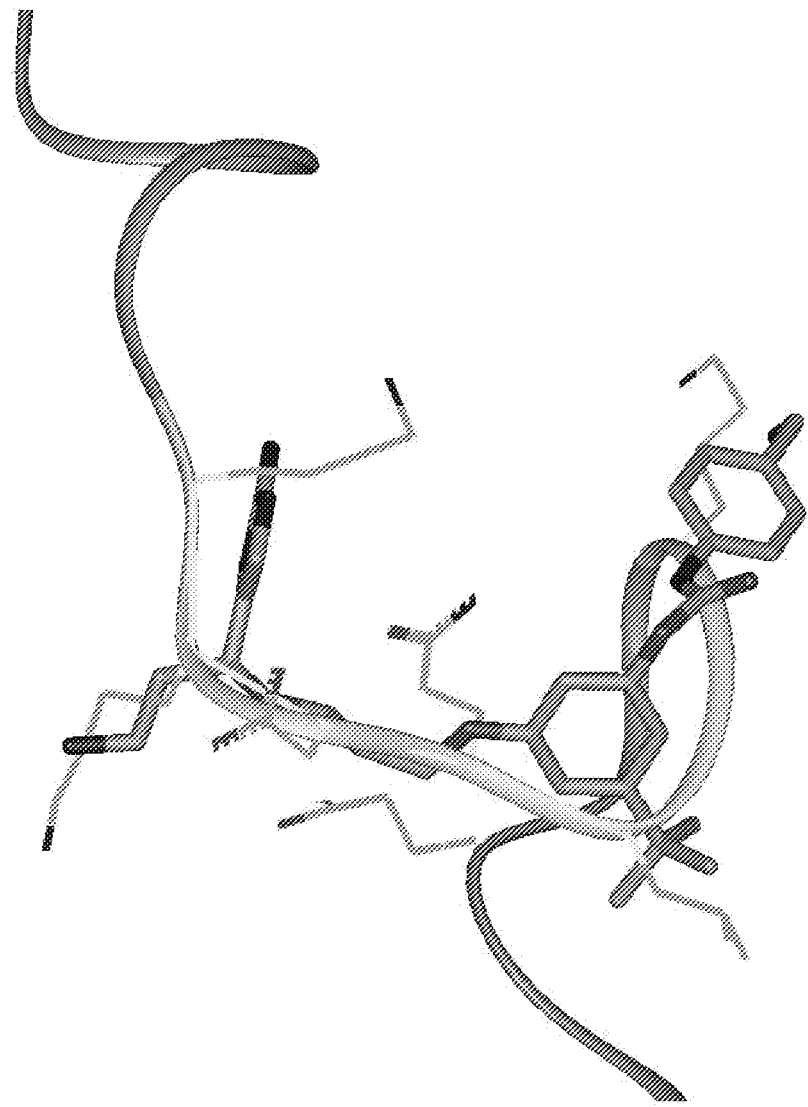
FIG. 16 illustrates the docking of an exemplary structure of this invention resulting from the exemplary synthesis scheme as illustrated in FIG. 14, into the binding pocket of alpha-synuclein, as discussed in detail the Examples, below.

The invention provides methods for the sold state synthesis of an alpha synuclein inhibitor, e.g., comprising the synthetic schemes as set forth in FIGS. 12 and 14.

In alternative embodiments, the peptides and polypeptides of this invention, e.g., the exemplary peptides and polypeptides of this invention such as SEQ ID NO:1 and SEQ ID NO:2, comprise "conservative amino acid substitutions", which are substitutions which do not result in a significant change in the activity or tertiary structure of a selected polypeptide or protein. In alternative embodiments, these substitutions replace a selected amino acid residue with a different residue having similar physico-chemical properties. Groupings of amino acids by physico-chemical properties are known to those of skill in the art. For example, in alternative embodiments, families of amino acid residues having similar side chains, which are well defined in the art, are substituted, and can include basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Pharmaceutical Compositions

The invention provides compositions as described herein, including pharmaceutical compositions, e.g., in the manufacture of medicaments for preventing, reversing, slowing or inhibiting protein aggregation, e.g., for treating diseases that are characterized by protein aggregation—including some degenerative neurological diseases such as Parkinson's disease.

In alternative embodiments, the compositions and analogs of the invention are formulated with a pharmaceutically acceptable carrier. In alternative embodiments, the pharmaceutical compositions of the invention can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

Therapeutic agents of the invention can be administered alone or as a component of a pharmaceutical formulation (composition). The compounds may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions and analogs of the invention include those suitable for oral/nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

Pharmaceutical formulations of this invention can be prepared according to any method known to the art for the manufacture of pharmaceuticals. Such drugs can contain sweetening agents, flavoring agents, coloring agents and preserving agents. A formulation can be admixtured with non-toxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, e.g., push-fit capsules made of gelatin, as well as soft, sealed capsules made of gelatin and a coating such as glycerol or sorbitol. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., a chimeric polypeptide or peptidomimetic of the invention) in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil-based pharmaceuticals are particularly useful for administration of the hydrophobic active agents of the invention, including compositions and analogs of the invention. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

In practicing this invention, the pharmaceutical compounds can also be administered by in intranasal, intraocular and intravaginal routes including suppositories, insufflation, powders and aerosol formulations (for examples of steroid inhalants, see Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In practicing this invention, the pharmaceutical compounds can be delivered by transdermally, by a topical route, formulated as applicator sticks, solutions, suspensions, emulsions, gels, creams, ointments, pastes, jellies, paints, powders, and aerosols.

In practicing this invention, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In practicing this invention, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and can be selected primarily based on fluid volumes, viscosities, body weight, and the like, in accordance with the particular mode of administration selected and the patient's needs.

For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

The pharmaceutical compounds and formulations of the invention can be lyophilized. The invention provides a stable lyophilized formulation comprising a composition of the invention, which can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. patent app. no. 20040028670.

Nanoparticles and Liposomes

The compositions and formulations of the invention can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587.

The invention also provides nanoparticles and liposomal membranes comprising compounds of this invention which target specific molecules, including biologic molecules, such as polypeptide, including cell surface polypeptides. Thus, in alternative embodiments, the invention provides nanoparticles and liposomal membranes targeting nerve cells, including dysfunctional cells or cells affected by an intracellular or extracellular protein aggregation.

In alternative embodiments, the invention provides nanoparticles and liposomal membranes comprising (in addition to comprising compounds of this invention) molecules, e.g., peptides or antibodies, that selectively target diseased, infected, dysfunctional and/or normal nerve or glial cells. In alternative embodiments, the invention provides nanoparticles and liposomal membranes to targeted receptors on nerve or glial cells. See, e.g., U.S. patent application publication no. 20060239968.

Thus, in one aspect, the compositions of the invention are specifically targeted for inhibiting, ameliorating and/or preventing (including slowing the progression of) degenerative neurological diseases related to or caused by aggregation, e.g., synuclein, beta-amyloid and/or tau protein aggregation.

The invention also provides nanocells to allow the sequential delivery of two different therapeutic agents with different modes of action or different pharmacokinetics, at least one of which comprises a composition of this invention. A nanocell is formed by encapsulating a nanocore with a first agent inside a lipid vesicle containing a second agent; see, e.g., Sengupta, et al., U.S. Pat. Pub. No. 20050266067. The agent in the outer lipid compartment is released first and may exert its effect before the agent in the nanocore is released. The nanocell delivery system may be formulated in any pharmaceutical composition for delivery to patients suffering from a diseases or condition as described herein, e.g., such as an individual with a degenerative neurological disease related to or caused by protein aggregation, e.g., synuclein, beta-amyloid and/or tau protein aggregation.

The invention also provides multilayered liposomes comprising compounds of this invention, e.g., for transdermal absorption, e.g., as described in Park, et al., U.S. Pat. Pub. No.

20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition of this invention.

A multilayered liposome of the invention may further include an antiseptic, an antioxidant, a stabilizer, a thickener, and the like to improve stability. Synthetic and natural antiseptics can be used, e.g., in an amount of 0.01% to 20%. Antioxidants can be used, e.g., BHT, erysorbate, tocopherol, astaxanthin, vegetable flavonoid, and derivatives thereof, or a plant-derived antioxidizing substance. A stabilizer can be used to stabilize liposome structure, e.g., polyols and sugars. Exemplary polyols include butylene glycol, polyethylene glycol, propylene glycol, dipropylene glycol and ethyl carbitol; examples of sugars are trehalose, sucrose, mannitol, sorbitol and chitosan, or a monosaccharides or an oligosaccharides, or a high molecular weight starch. A thickener can be used for improving the dispersion stability of constructed liposomes in water, e.g., a natural thickener or an acrylamide, or a synthetic polymeric thickener. Exemplary thickeners include natural polymers, such as acacia gum, xanthan gum, gellan gum, locust bean gum and starch, cellulose derivatives, such as hydroxy ethylcellulose, hydroxypropyl cellulose and carboxymethyl cellulose, synthetic polymers, such as poly-acrylic acid, poly-acrylamide or polyvinylpyrollidone and polyvinylalcohol, and copolymers thereof or cross-linked materials.

Liposomes can be made using any method, e.g., as described in Park, et al., U.S. Pat. Pub. No. 20070042031, including method of producing a liposome by encapsulating a therapeutic product comprising providing an aqueous solution in a first reservoir; providing an organic lipid solution in a second reservoir, wherein one of the aqueous solution and the organic lipid solution includes a therapeutic product; mixing the aqueous solution with said organic lipid solution in a first mixing region to produce a liposome solution, wherein the organic lipid solution mixes with said aqueous solution so as to substantially instantaneously produce a liposome encapsulating the therapeutic product; and immediately thereafter mixing the liposome solution with a buffer solution to produce a diluted liposome solution.

The invention also provides nanoparticles comprising compounds of this invention to deliver a composition of the invention as a drug-containing nanoparticles (e.g., a secondary nanoparticle), as described, e.g., in U.S. Pat. Pub. No. 20070077286. In one embodiment, the invention provides nanoparticles comprising a fat-soluble drug of this invention or a fat-solubilized water-soluble drug to act with a bivalent or trivalent metal salt.

For example, in one embodiment, compositions and formulations of the invention are delivered by the use of liposomes having rigid lipids having head groups and hydrophobic tails, e.g., as using a polyethyleneglycol-linked lipid having a side chain matching at least a portion the lipid, as described e.g., in US Pat App Pub No. 20080089928. In another embodiment, compositions and formulations of the invention are delivered by the use of amphoteric liposomes comprising a mixture of lipids, e.g., a mixture comprising a cationic amphiphile, an anionic amphiphile and/or neutral amphiphiles, as described e.g., in US Pat App Pub No. 20080088046, or 20080031937. Amphoteric liposomes of the invention can comprise an active ingredient and at least one amphipathic cationic lipid, at least one amphipathic anionic lipid, and at least one neutral lipid, e.g., as described in U.S. Pat. No. 7,371,404.

In another embodiment, compositions and formulations of the invention are delivered by the use of liposomes comprising a polyalkylene glycol moiety bonded through a thioether group and an antibody also bonded through a thioether group to the liposome, as described e.g., in US Pat App Pub No. 20080014255. In another embodiment, compositions and formulations of the invention are delivered by the use of liposomes comprising glycerides, glycerophospholipids, glycerophosphinolipids, glycerophosphonolipids, sulfolipids, sphingolipids, phospholipids, isoprenolides, steroids, stearines, sterols and/or carbohydrate containing lipids, as described e.g., in US Pat App Pub No. 20070148220.

In one embodiment, compositions and formulations of the invention are delivered by the use of liquid-crystalline multi-molecular aggregates comprising a plurality of amphiphilic molecules dispersed in an aqueous solution, e.g., as described in U.S. Pat. No. 7,368,129.

In one embodiment, compositions and formulations of the invention are delivered to the respiratory tract of an individual via inhalation, e.g., using a nebulized liposomal aerosol, e.g., comprising a dilauroylphosphatidylcholine liposome, e.g., as described in U.S. Pat. No. 7,348,025.

In one embodiment, compositions and formulations of the invention are delivered via their formulation into a unimolecular multi-arm block copolymer comprising, e.g., a hydrophilic polymer segment such as poly(alkylene glycols), copolymers of ethylene glycol and propylene glycol, poly (olefinic alcohol), poly(vinylpyrrolidone), poly(hydroxy-alkylmethacrylamide), poly(hydroxyalkylmethacrylate), poly(saccharides), poly(.alpha.-hydroxy acid), poly(vinyl alcohol), polyphosphazene, polyoxazoline and poly(N-acryloylmorpholine), and the like, e.g., as described in U.S. Pat. App. Pub. No. 20080069902.

In one embodiment, compositions and formulations of the invention are delivered via solid, biodegradable in-situ implants; e.g., by administering a liquid pharmaceutical composition comprising an effective amount of a biocompatible, water-insoluble, biodegradable polymer and an effective amount of a peptide or polypeptide of this invention. In one aspect, a peptide or polypeptide of this invention covalently modified with one or more lipophilic or amphiphilic moieties, which are dissolved or dispersed in a biocompatible, water-soluble organic solvent, e.g., as described in U.S. Pat. App. Pub. No. 20080020016. Compositions and formulations of the invention can be delivered using any injectable liquid biodegradable polymeric composition, e.g., as an in situ forming implant to deliver a peptide or polypeptide of this invention, e.g., as described in U.S. Pat. Nos. 6,565,874; 6,528,080; 6,461,631; 6,395,293; 6,355,657; 6,261,583; 6,143,314; 5,990,194; 5,945,115; 5,792,469; 5,780,044; 5,759,563; 5,744,153; 5,739,176; 5,736,152; 5,733,950; 5,702,716; 5,681,873; 5,599,552; 5,487,897; 5,340,849; 5,324,519; 5,278,202; 5,278,201; 4,938,763.

In one embodiment, compositions and formulations of the invention are delivered via transdermal systems for sustained delivery, e.g., as described in U.S. Pat. App. Pub. No. 20070287949, Levin et al. For example, compositions and formulations of the invention can be delivered via transdermal patches, and/or via an apparatus that generates microchannels in the skin of a subject in combination with a transdermal patch, see e.g., Levin et al.

In one embodiment, compositions and formulations of the invention are delivered via orally administered formulations, e.g., as described in U.S. Pat. Nos. 5,008,114; 5,505,962; 5,641,515; 5,681,811; 5,700,486; 5,766,633; 5,792,451; 5,853,748; 5,972,387; 5,976,569; and 6,051,561.

Therapeutically Effective Amount and Dose

The compositions and formulations of the invention can be administered for prophylactic and/or therapeutic treatments. In therapeutic applications, in alternative embodiments, compositions are administered to a subject already suffering from a condition, infection or disease in an amount sufficient to cure, alleviate or partially arrest the clinical manifestations of the condition, infection or disease and its complications (a "therapeutically effective amount"). In alternative embodiments of the methods of the invention, a pharmaceutical composition is administered in an amount sufficient to treat, prevent or ameliorate (including slowing the progression of) degenerative neurological diseases related to or caused by protein aggregation, e.g., synuclein, beta-amyloid and/or tau protein aggregation. In one aspect, compositions and methods of this invention are used to treat, prevent or ameliorate (including slowing the progression of) Parkinson's disease, Alzheimer's Disease (AD), Lewy body disease (LBD) and Multiple system atrophy (MSA).

The amount of pharmaceutical composition of the invention adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on the dosage and frequency as required and tolerated by the patient. The formulations should provide a sufficient quantity of active agent to effectively prevent, reverse, slow or inhibit a degenerative neurological disease related to or caused by protein aggregation, e.g., synuclein, beta-amyloid and/or tau protein aggregation, such as Parkinson's disease, Alzheimer's Disease (AD), Lewy body disease (LBD) and Multiple system atrophy (MSA). For example, an exemplary pharmaceutical formulation for oral administration of chimeric polypeptide of the invention is in a daily amount of between about 0.1 to 0.5 to about 20, 50, 100 or 1000 or more ug per kilogram of body weight per day. In an alternative embodiments, dosages are from about 1 mg to about 4 mg per kg of body weight per patient per day are used. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

In an alternative embodiment, compositions of this invention are used to treat dementia and dementia-type disorders related to protein aggregation, and any systems and/or methods for analyzing and assessing dementia and dementia-type disorders can be used to assess the efficacy of a composition of this invention on an individual, e.g., to determine and calibrate a dose or a dosage regimen; for example, by integrating the use of electroencephalography (EEG), neuropsychological or cognitive testing data, and cardiovascular risk factor data. In practicing this invention, systems and methods for early detection of dementia, including Alzheimer's disease (AD), Parkinson's disease (PD), vascular dementia (VAD), mixed dementia (AD and VAD), MCI, and other dementia-type disorders can be used. Accurate detection of mild dementia and some cases of mild cognitive impairment in addition to the detection of moderate to severe dementia can be assessed using any method or protocol, e.g., as described in U.S. Pat. App. Pub. No. 20070299360.

Drug Combinations and Co-Administrations

The compositions and formulations of the invention can further comprise other drugs or pharmaceuticals, e.g., other compositions for treating or palliative for a degenerative neurological disease related to or caused by protein aggregation, e.g., synuclein, beta-amyloid and/or tau protein aggregation, e.g., Parkinson's disease, Alzheimer's Disease (AD), Lewy body disease (LBD) and Multiple system atrophy (MSA) and related symptoms or conditions. For example, the methods and/or compositions and formulations of the invention can be co-formulated with and/or co-administered with antibiotics (e.g., antibacterial or bacteriostatic peptides or proteins), e.g., those effective against gram negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof.

The compositions and formulations of the invention can be co-administered with an Alzheimer's disease, or a Parkinson's disease, etc. treatment or palliative drug, such as tacrine (Cognex), donepezil (Aricept), rivastigmine (Exelon) galantamine (Reminyl), physostigmine, neostigmine, Icopezil (CP-118954, 5,7-dihydro-3-[2-[1-(phenylmethyl)-4-piperidinyl]ethyl]-6H-pyrrolo-[4,5-f-]-1,2-benzisoxazol-6-one maleate), ER-127528 (4-[(5,6-dimethoxy-2-fluoro-1-indanon)-2-yl]methyl-1-(3-fluorobenzyl)pipe-ridine hydrochloride), zanapezil (TAK-147; 3-[1-(phenylmethyl)piperidin-4-yl]-1-(2,3,4,5-tetrahydro-1H-1-benzazepin-8-yl)-1-propane fumarate), Metrifonate (T-588; (−)-R-.alpha.-[[2-(dimethylamino)ethoxy]methyl]benzo[b]thiophene-5-methanol hydrochloride), FK-960 (N-(4-acetyl-1-piperazinyl)-p-fluorobenzamide-hydrate), TCH-346 (N-methyl-N-2-pyropinyldibenz[b,f]oxepine-10-methanamine), SDZ-220-581 ((S)-.alpha.-amino-5-(phosphonomethyl)-[1,1'-biphenyl]-3-propionic acid), memantine (Namenda/Exiba) and 1,3,3,5,5-pentamethylcyclohexan-1-amine (Neramexane), tarenflurbil (Flurizan), tramiprosate (Alzhemed), clioquinol, PBT-2 (an 8-hydroxyquinilone derivative), 1-(2-(2-Naphthyl)ethyl)-4-(3-trifluoromethylphenyl)-1,2,3,6-tetrahydropyr-idine, Huperzine A, posatirelin, leuprolide or derivatives thereof, ispronicline, (3-aminopropyl)(n-butyl)phosphinic acid (SGS-742), N-methyl-5-(3-(5-isopropoxypyridinyl))-4-penten-2-amine (ispronicline), 1-decanaminium, N-(2-hydroxy-3-sulfopropyl)-N-methyl-N-octyl-, inner salt (zt-1), salicylates, aspirin, amoxiprin, benorilate, choline magnesium salicylate, diflunisal, faislamine, methyl salicylate, magnesium salicylate, salicyl salicylate, diclofenac, aceclofenac, acemetacin, bromfenac, etodolac, indometacin, nabumetone, sulindac, tolmetin, ibuprofen, carprofen, fenbufen, fenoprofen, flurbiprofen, ketoprofen, ketorolac, loxoprofen, naproxen, tiaprofenic acid, suprofen, mefenamic acid, meclofenamic acid, phenylbutazone, azapropazone, metamizole, oxyphenbutazone, sulfinprazone, piroxicam, lornoxicam, meloxicam, tenoxicam, celecoxib, etoricoxib, lumiracoxib, parecoxib, rofecoxib, valdecoxib, nimesulide, arylalkanoic acids, 2-arylpropionic acids (profens), N-arylanthranilic acids (fenamic acids), pyrazolidine derivatives, oxicams, COX-2 inhibitors, sulphonanilides, essential fatty acids, and/or Minozac (2-(4-(4-methyl-6-phenylpyridazin-3-yl)piperazin-1-yl)pyrimidine dihydrochloride hydrate).

Kits and Libraries

The invention provides kits comprising compositions (including the pharmaceutical compositions and formulations) of this invention and methods of the invention, instructions (regarding the methods of the invention to treat, prevent or ameliorate (including slowing the progression of) degenerative neurological diseases related to or caused by aggregation, e.g., synuclein, beta-amyloid and/or tau protein aggregation), or any combination thereof. As such, kits, nanoparticles and the like are provided herein.

The invention will be further described with reference to the following examples; however, it is to be understood that the invention is not limited to such examples.

EXAMPLES

Example 1

AA 53 to 66 of SYN is Important in Mediating SYN Aggregation

This example presents data demonstrating that exemplary compounds of this invention are effective in blocking or interfering with protein aggregation, or more specifically, blocking or interfering alpha-synuclein (SYN) aggregation.

Based on studies of the structure of alpha-synuclein (SYN) and how the process of aggregation leads to the formation of toxic oligomers, this invention determined that among others, the SYN region between amino acid residue 53 to 66 is important in mediating the aggregation of SYN, as illustrated in FIG. 1. The SYN molecule can form dimers under physiological conditions, however these dimers are usually oriented in a head to tail conformation (N-term of one SYN with the C-term of the other SYN); see FIG. 1.

The human "alpha-synuclein isoform NACP140" has been described as having the sequence (see e.g., Ueda (1993) Proc. Natl. Acad. Sci. USA 90 (23):11282-11286; Campion (1995) Genomics 26 (2):254-257; Chen (1995) Genomics 26 (2): 425-427):

membrane-contacting N-terminal (n-term) regions are designated by boxes and C-terminal (c-term) regions by lines, as viewed perpendicular to the membrane surface. In the lower panels, various dockings are illustrated: for example, the second α-syn molecule (α-syn 2) docks to the first (α-syn 1), followed by docking of the third α-syn molecule (α-syn 3) to the second, etc., considering minimal docking energies from all possible docking positions. FIG. 1 bottom panel illustrates a non-propagating conformation (head-to-tail) of two α-syn monomers that prevents low-energy docking of additional monomers. FIG. 1 bottom panel illustrates a propagating conformation that allows low energy docking of additional monomers added sequentially (in the direction of the arrow).

Molecular modeling of dimer, tetramer, and hexamer: Multimers can be formed by docking of α-syn monomers to α-syn propagating dimers, or by addition of α-syn dimers to α-syn propagating dimers, with either scenario resulting in the same final hexamer structure.

Figure 2:
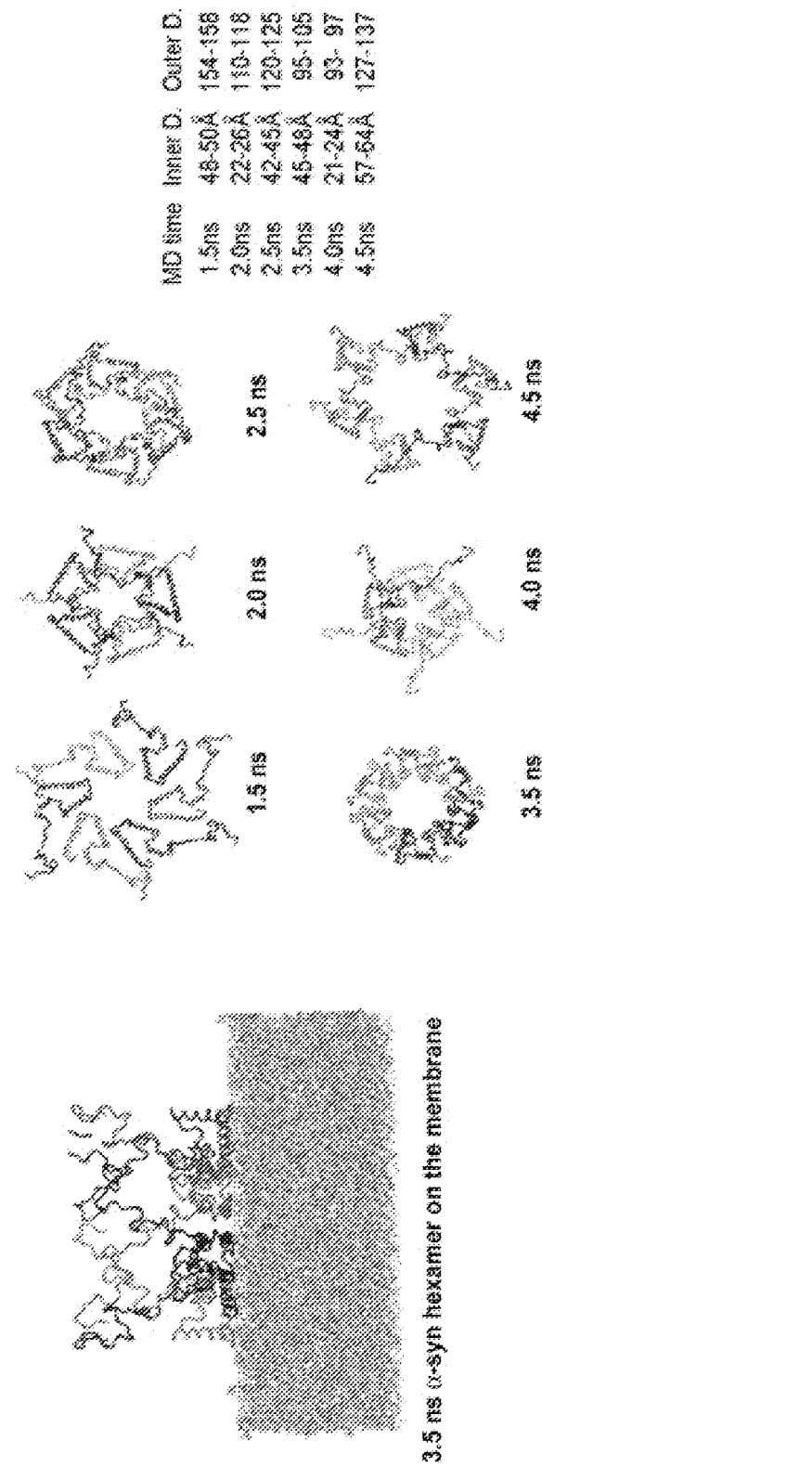
FIG. 2 illustrates molecular dynamics studies of the α-syn oligomers in the membrane forming ring-like structures, as discussed in detail the Examples, below.
Figure 3:
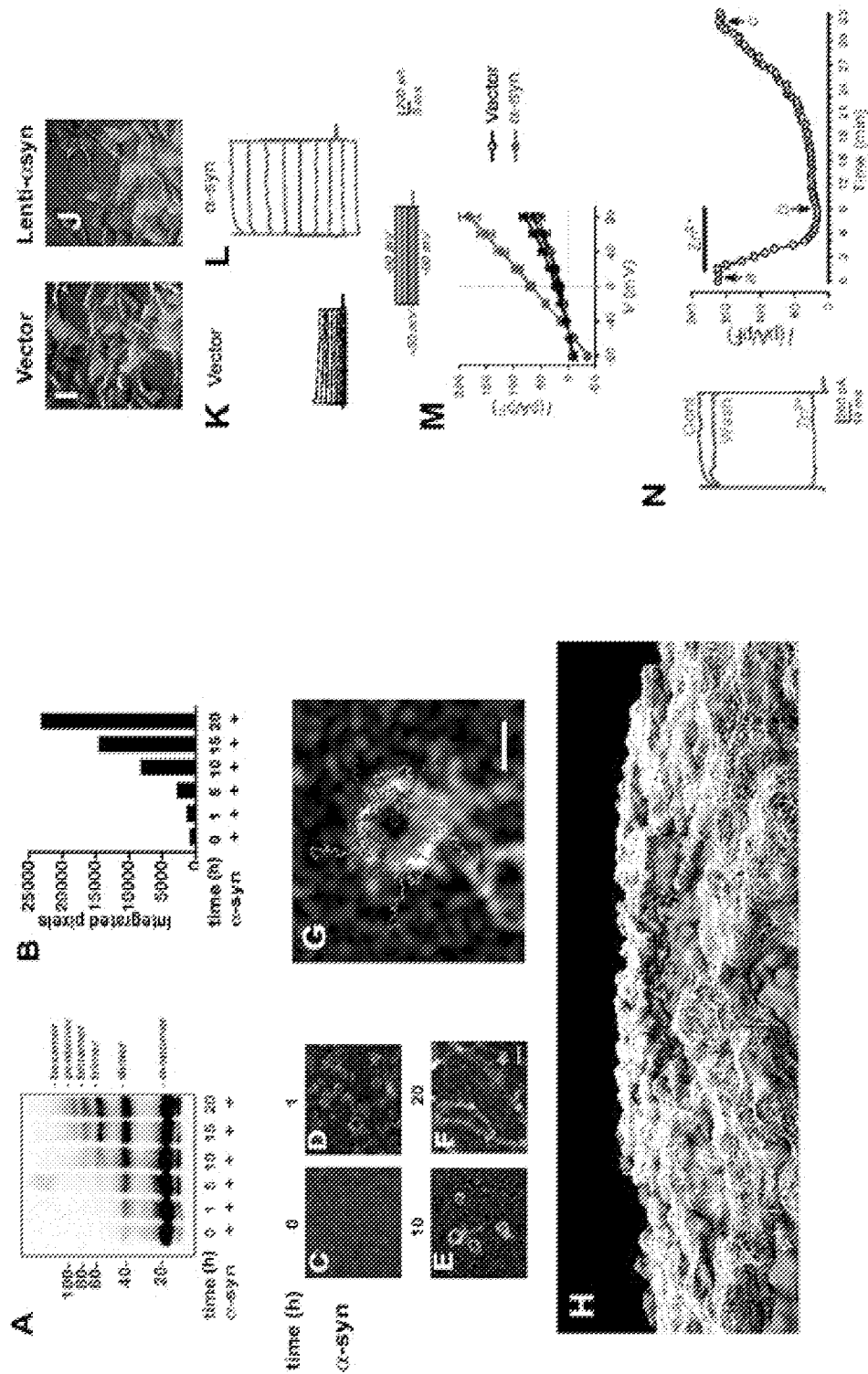
FIG. 3 illustrates SYN aggregation and oligomerization in vitro results in ring-like formation and abnormal electric currents in cell lines overexpressing α-syn, as discussed in detail the Examples, below.

Under pathological conditions it is believed that the conformation of SYN changes and dimers that aggregate head to head facilitate the incorporation of other SYN monomers leading to the formation of pentamers, hexamers and heptamers with a ring structure, as illustrated in FIGS. 1 and 2. These oligomers could in turn embed in the membrane and form pores or channel-like structures that conduct abnormal currents in the neurons, as illustrated in FIGS. 2 and 3. Abnormal calcium flux resulting from these channels may lead to neuronal dysfunction and eventually cell death, see data set forth in see FIG. 3.

FIG. 2 illustrates molecular dynamics studies of the α-syn oligomers in the membrane forming ring-like structures. FIG. 2(A) (left illustration) illustrates the final configuration of the hexamer after 3.5 ns on the membrane, as a side view. FIG. 2(B) (left illustration) illustrates the modeling of multimers at various time points between 1.5 and 4.5 ns, as a top view. The table to the right margin indicates the inner diameters (ID) and outer diameters (OD) of the multimers created from the conformers obtained at the various molecular dynamics (MD) time points.

FIG. 3 illustrates SYN aggregation and oligomerization in vitro results in ring-like formation and abnormal electric currents in cell lines overexpressing α-syn. FIG. 3A illustrates in vitro cell-free aggregation of α-syn monomers into dimers, trimers, tetramers, pentamers and hexamers over time. FIG. 3B illustrates Semi-quantitative analysis of levels of α-syn multimers over time. FIG. 3C, FIG. 3D, FIG. 3E and FIG. 3F: illustrate electron microscopy analysis of α-syn aggregation over time into ring-like structures and fibrils; FIG. 3C, FIG. 3D, FIG. 3E and FIG. 3F also illustrate electron microscopy analysis demonstrating reduction in α-syn aggregation over time; in FIG. 3F bar=20 nm. FIG. 3G illustrates superimpo- (SEQ ID NO: 3)
```
  1 mdvfmkglsk akegvvaaae ktkqgvaeaa gktkegvlyv gsktkegvvh gvatvaektk 61 eqvtnvggav vtgvtavaqk tvegagsiaa atgfvkkdql gkneegapqe giledmpvdp 121 dneayempse egyqdyepea
```

FIG. 1 illustrates molecular dynamics studies of the critical sites in the α-syn dimers that mediate aggregation leading to oligomer formation. FIG. 1 illustrates specific inter-molecular interactions between two head-to-head α-syn monomers over time (4 ns), and demonstrates the critical sites of interaction (rectangles) toward the formation of propagating dimer. In the sequence illustration of α-syn in the upper panel, sition of α-syn pentamer (4.5 ns) onto the ring-like structure detected by electron microscopy; bar=10 nm. Figure H illustrates modeling of the embedded α-syn complex in the membrane over time: a top view, at the level of the uppermost membrane-associated atom, of the embedded portion of the α-syn pentamer (350 ps) on the POPC membrane; white=α-syn pentamer; green=membrane phospholipids. Note the penetration of the pentamer into the membrane and the exposed membrane in the center of the α-syn ring-like structure.

FIG. 3I and FIG. 3J are micrograph illustrations of HEK293T cells, showing that cells transduced with lentiviral vectors encoding α-syn and GFP express comparable protein levels. FIG. 3K, FIG. 3L and FIG. 3M graphically illustrate data showing representative currents elicited by depolarizing the cells from a holding potential of −50 mv to a series of test potentials ranging from −80 to +80 mv, and corresponding current-voltage relationship (E; means±SE) in transduced cells. Cells expressing α-syn display a significant increase in ion currents. FIG. 3N left panel graphically illustrates representative currents at +80 mv (left panel) before (Cont), during ($Zn^{2+}$) and after (Wash) application of 500 µM $Zn^{2+}$. FIG. 3N, right panel, graphically illustrates the time course of the change in current density before, during, and after extracellular application of $Zn^{2+}$. The arrows correspond to the currents shown in the left panel (Cont, a; $Zn^{2+}$, b; and Washout, c). The increased currents in cells expressing α-syn are attenuated by $Zn^{2+}$.

SYN is known to be an intra-cellular molecule; the native SYN molecule is cytoplasmic, and has been shown that the toxic multimer most likely is located in the plasma membrane where it can be accessed by a SYN blocking compound of this invention, see FIGS. 2 and 3. In addition to blocking SYN dimers and oligomers, compounds of this invention may block the rings and pore-like structures, interfering with the abnormal channel current activity, as illustrated in see FIG. 3. Also, in one embodiment, compounds of the invention may be endocytosed.

Example 2

Peptide and Cyclic Peptidomimetic Compounds Prevent Protein Aggregation

This example presents data demonstrating that exemplary peptides of this invention are effective in blocking or interfering with protein aggregation, or more specifically, blocking or interfering alpha-synuclein (SYN) aggregation. This example presents data demonstrating that exemplary peptides of this invention can prevent the formation of toxic SYN aggregates.

Figure 4:
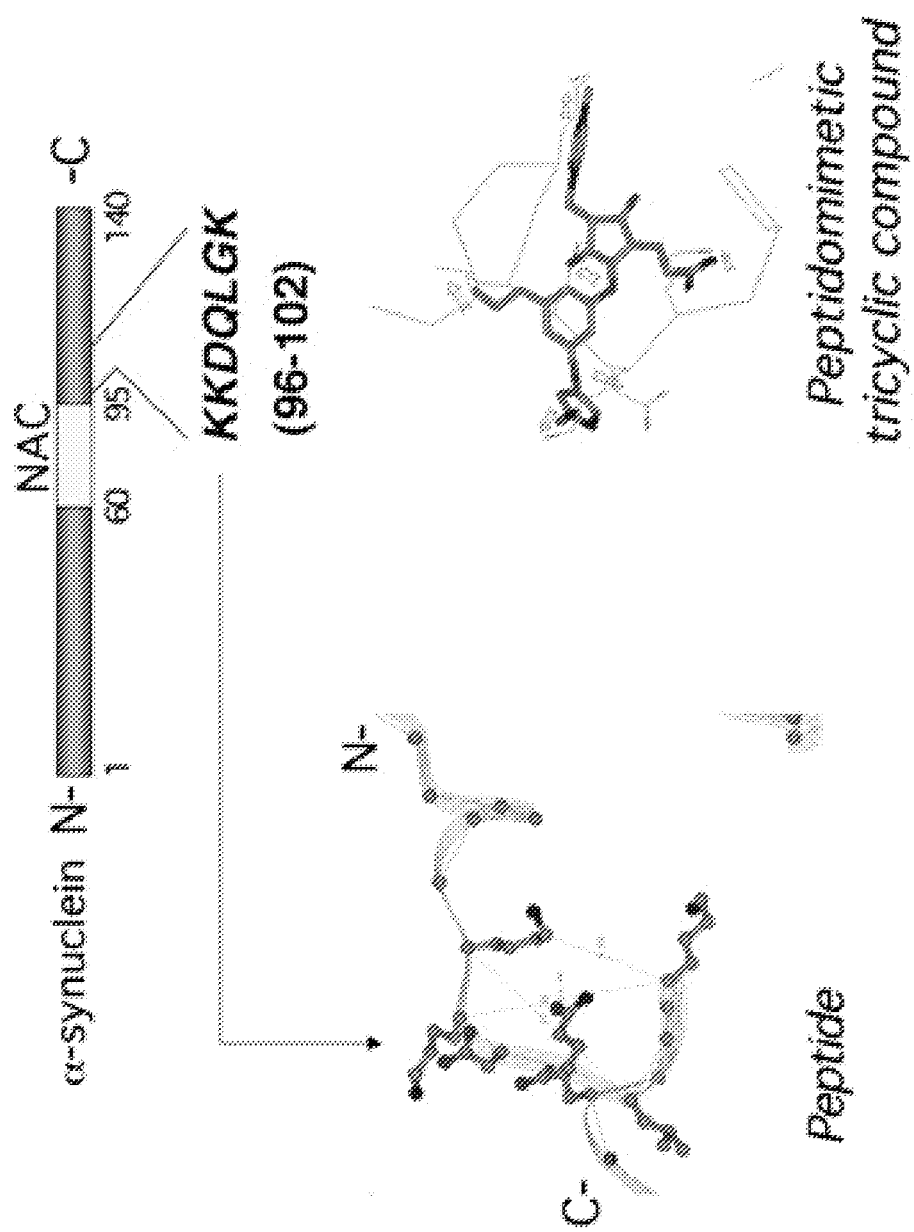
FIG. 4 upper panel illustrates a schematic representation of the site within α-syn that is suitable for blocking with peptides and peptidomimetic compounds of this invention; about a dozen overlapping peptides within the critical region in the c-terminus were designed and tested in silico for the ability to clock α-syn propagation; the lower left panel of FIG. 4 illustrates that the in silico analysis has the exemplary peptide of this invention peptide KKDQLGK (SEQ ID NO:1) as the most effective α-syn blocking peptide; and the lower right panel of FIG. 4 illustrates in silico analysis binding of a peptidomimetic tricyclic compound of this invention to α-syn.

The invention provides peptides, including KKDQLGK (SEQ ID NO:1) and corresponding tricyclic (WW-138) and bicyclic peptidomimetic compounds to prevent, reverse or slow the formation of toxic SYN aggregates, and can be used in pharmaceutical compositions as a novel therapy for PD and other neurodegenerative disorders with SYN aggregation, see FIG. 4.

FIG. 4 illustrates a schematic representation of the site within α-syn that is suitable for blocking with peptides and peptidomimetic compounds; about a dozen overlapping peptides within the critical region in the c-terminus were designed and tested in silico for the ability to clock α-syn propagation; as the figure indicates, the peptide having the sequence KKDQLGK (SEQ ID NO:1) was the most effective.

Figure 5:
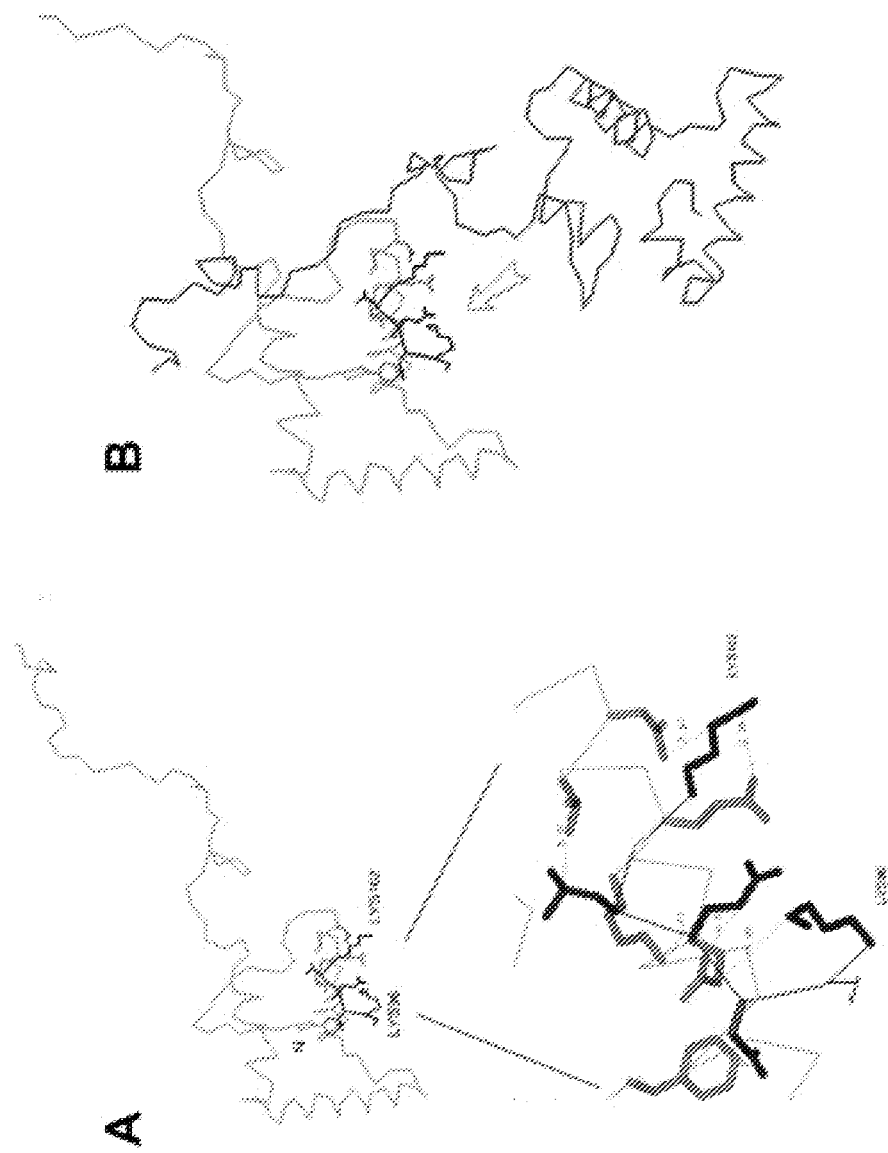
FIG. 5 illustrates a molecular representation of a model for an exemplary peptide of this invention blocking of α-syn dimer aggregation, as discussed in detail the Examples, below.

While the invention is not limited by any particular mechanism of action, the peptide and the cyclic peptidomimetic compounds dock on a critical region of SYN preventing further aggregation; see FIGS. 4 and 5. While the invention is not limited by any particular mechanism of action, FIG. 4 illustrates an exemplary model of the invention, site of activity and steps for developing peptidomimetic compounds that block SYN aggregation.

While the invention is not limited by any particular mechanism of action, FIG. 5 illustrates an exemplary model for the mode of action and site of the peptide that blocks SYN aggregation and pathological dimer formation. FIG. 5 illustrates a molecular representation of a model for an exemplary peptide of this invention blocking of α-syn dimer aggregation. FIG. 5A illustrates a representation with side chains of the exemplary KKDQLGK (SEQ ID NO:1) peptide of the invention docking to the c-terminus of α-syn. FIG. 5B illustrates that a docked peptide of this invention blocks dimer formation.

Figure 6:
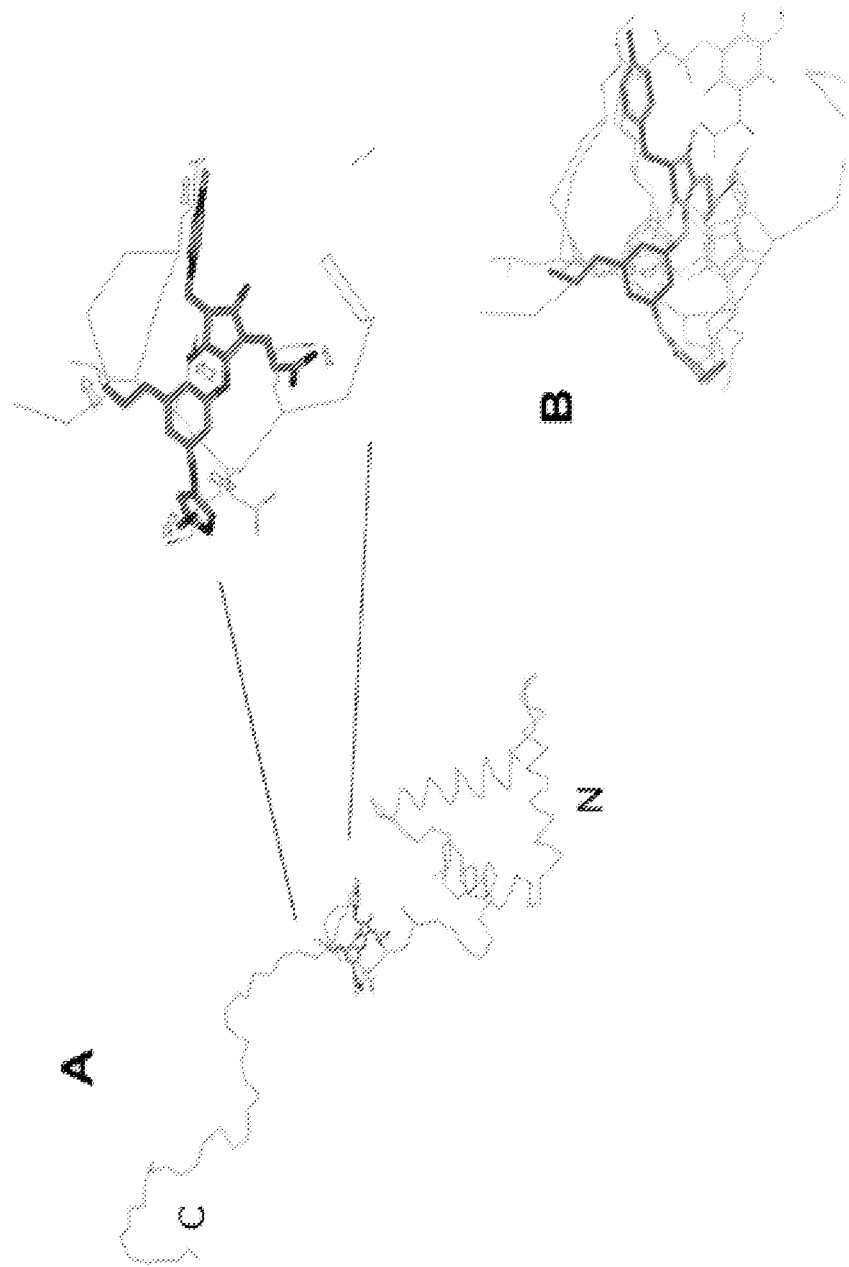
FIG. 6 illustrates a molecular modeling of a peptidomimetic bicyclic compound of this invention docking to α-syn.

While the invention is not limited by any particular mechanism of action, FIG. 6 illustrates an exemplary model for the equivalent site and mode of action of a peptidomimetic tricyclic compound that blocks SYN aggregation. FIG. 6 illustrates a molecular modeling of a peptidomimetic bicyclic compound of this invention docking to α-syn. FIG. 6A illustrates a representation of peptidomimetic compound docking to the c-terminus of α-syn. FIG. 6B illustrates that a docked peptidomimetic compound of this invention blocks dimer formation.

Computer simulations and calculations were used to design exemplary compositions of the invention, including the exemplary peptide KKDQLGK (SEQ ID NO:1) (see FIGS. 4 and 5) and the exemplary tricyclic peptidomimetic compound, and the exemplary bicyclic peptidomimetic compound, and all can prevent the formation of toxic SYN aggregates.

Figure 7:
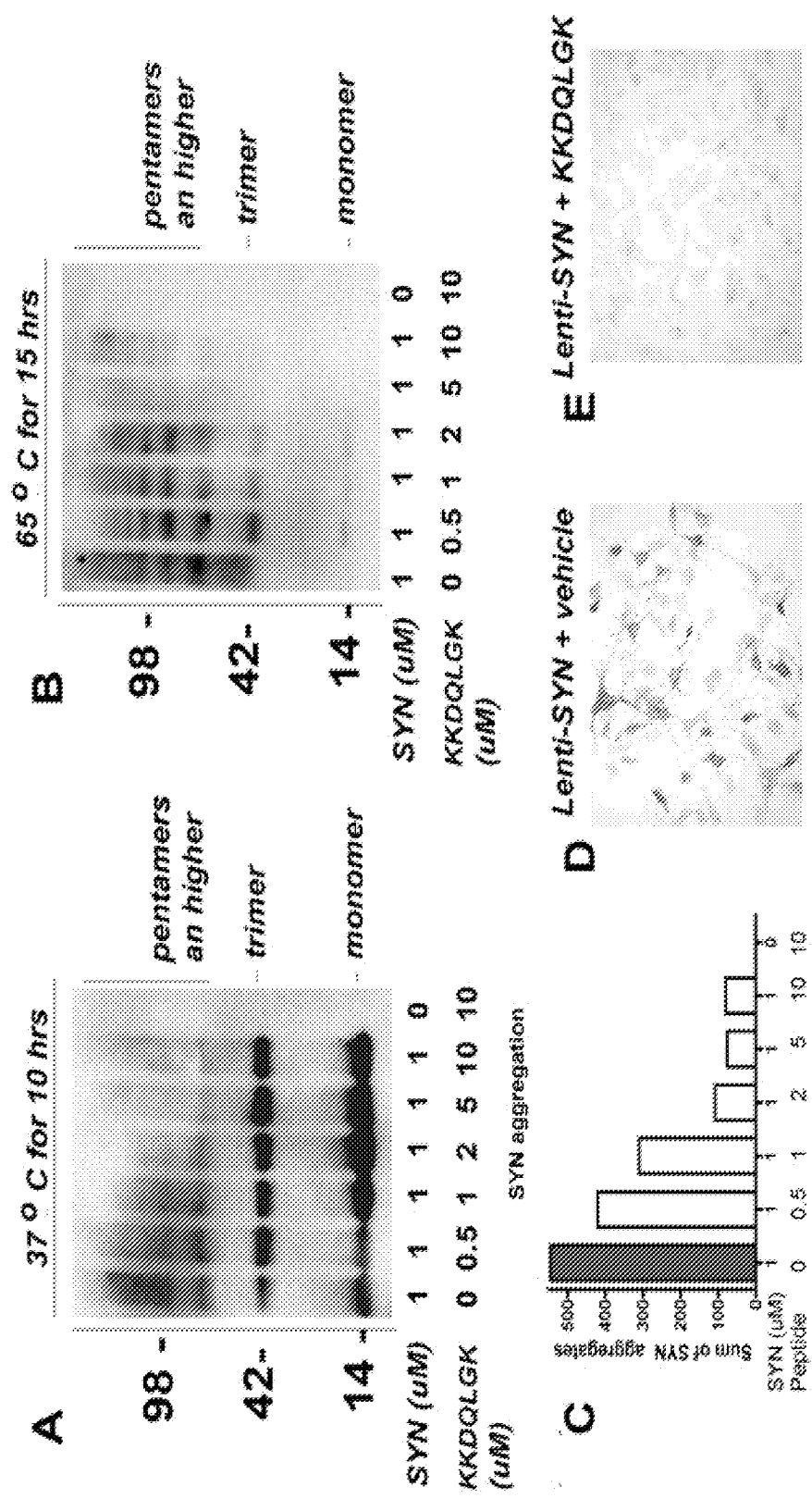
FIG. 7 illustrates in vitro studies showing that the peptide blocks of α-syn dimer aggregation, as discussed in detail the Examples, below.

FIG. 7 illustrates in vitro studies showing that the peptide blocks of α-syn dimer aggregation. FIG. 7A FIG. 7B illustrate cell free immunoblot assays showing reduced aggregation at 37° C. and 65° C. using the exemplary peptide of this invention (96-102) KKDQLGK peptide, (SEQ ID NO:1); and FIG. 7C graphically illustrates this data. FIG. 7D and FIG. 7E illustrate that neuronal cultures overexpressing α-syn show reduced accumulation upon treatment with the exemplary KKDQLGK peptide of this invention (SEQ ID NO:1) at 1 uM (with peptide; FIG. 7E), as compared to control, with vehicle only (no peptide; FIG. 7D).

These data demonstrate that compositions of the invention can be used as novel therapies for Parkinson's Disease (PD) and other neurodegenerative disorders where proteins, e.g., SYN, aggregate.

Example 3

Design of Peptides and Peptidomimetics of this Invention

While the invention is not limited by any particular mechanism of action, the invention can work by blocking the formation of head to head SYN dimers and by blocking further incorporation of SYN monomers and the formation of the rings; see FIGS. 1 to 5. For this purpose a series of peptides homologous to small regions of SYN that bind to the critical region of SYN and block further aggregation (see FIGS. 5 and 6) were designed and tested. They were tested in a cell free system these peptides with the appropriate controls (including smaller and larger peptides, amino acid (aa) substitutions, scrambled sequence). It was found that amino acids 57-65, i.e., the exemplary peptide of the invention EKTKEQVTN (SEQ ID NO:2), or 96-102, i.e., the exemplary peptide of the invention KKDQLGK (SEQ ID NO:1) were the most effective at blocking SYN aggregation. The exemplary peptide of the invention KKDQLGK (SEQ ID NO:1) binds to the 4 ns conformer of SYN in a head to head orientation.

Then based on the peptide structure and its relationship with the SYN molecule, a peptidomimetic compound was designed (see FIGS. 5 and 6). For this purpose, the various residues of the peptide were deconstructed into specific fragments of residues which contain hydrogen bond donor, hydrogen bond acceptors, regions of polar interactions and most important regions of hydrophobic interactions (see FIG. 5). Then the dimensions of the peptide and the small organic compound were calculated and compared. Of special relevance are the relative dimensions between the hydrogen bonding residues and the hydrophobic residues. Then the organic molecule having no obvious metabolic liabilities or "bad groups" and one, which have only limited flexibility, are re-constructed accordingly. This limited flexibility is very important to ensure later protein interaction specific binding. Based on the fragments in the reconstruction phase a molecule is designed that can be synthesized in about 5-7 steps. Finally, simulations and modifications are perform to ensure that the small compound fits within the critical site of the SYN molecule within 2 to 3 Angstroms.

Example 4

Exemplary Peptidomimetic Tricyclic Compounds of the Invention

Following the procedure in Example 3, the exemplary peptidomimetic tricyclical compounds of the invention were designed: [3-(2-amino-4-(2-aminoethyl)thiazol-5-yloxy)-5-isobutylphenyl 4-(aminomethyl)phenylcarbamate]; derived from structure based design that block SYN aggregation was generated. This is a simple structure that can be used to do many elaborations for making any number of analogs and even classes of analogs. This compound of the invention is predicted to interact in a restricted region of SYN similar to the exemplary peptide of the invention KKDQLGK (SEQ ID NO:1) (the "96 to 102 peptide"); see FIGS. 5 and 6). There are no covalent interactions or crosslinking, but rather hydrogen bonding, polar and hydrophobic interactions. The total binding energy of the molecule to the SYN should be at least 10-15 kacl/mole.

Another exemplary composition used on methods of this invention has a structure based on a design compound that blocks SYN aggregation through a similar mechanism: the bicyclic compound 8-(4-aminobutylsulfonyl)-6-(3-aminopropyl)-3-isobutyl-4,7-dioxooctahydro-1H-pyrimido[1,2-a]pyrazin-1-yl 3-aminopropanoate. This compound can be synthesized in less steps than tricyclic compound. Analogues and derivatives can be generated for testing and screening in vitro.

Example 5

Inhibition of SYN Accumulation with an Exemplary Peptide of this Invention

This example describes data demonstrating the efficacy of polypeptides and peptides of this invention in inhibiting polypeptide, e.g., SYN, aggregation.

The peptides of the invention were tested in a cell free system with the appropriate controls (smaller and larger peptides, amino acid (aa) substitutions, scrambled sequence). For this purpose recombinant SYN (10 uM) was incubated at 37 and 65 degrees C. for 0, 4, 6, 12 and 24 with the peptides at 0, 1 and 10 uM. Control experiments where performed with beta and gamma-synuclein as well as with a mutant SYN molecule that cannot bind the peptide. The mixture was run in a gel, followed by immunoblot testing with SYN antibodies.

The B103 neuronal cell line was infected with a lentivirus expressing SYN (wildtype) or GFP (control) and cells expressing SYN were exposed to the peptides at 0, 1 and 10 uM for 24 hrs. Cells were assayed for SYN aggregation by immunoblot, neurite outgrowth and survival. By immunoblot, compared to controls, the KKDQLGK (SEQ ID NO:1) was the most effective at blocking SYN aggregation both in the in vitro cell free and neuronal cell based systems (see FIG. 7). The peptide KKDQLGK (SEQ ID NO:1) and control peptides can be injected into the brain of SYN transgenic (tg) mice to test for in vivo effects.

Example 6

In Vivo Experiments Demonstrating the Efficacy of Peptides of this Invention

This example in vivo protocols for demonstrating the efficacy of polypeptides and peptides of this invention in inhibiting polypeptide, e.g., SYN, aggregation.

The exemplary peptidomimetic tricyclical compound of the invention [3-(2-amino-4-(2-aminoethyl)thiazol-5-yloxy)-5-isobutylphenyl 4-(aminomethyl)phenylcarbamate]; see FIG. 4, and its derivatives can be chemically synthesized. These compounds can be tested in the in vitro cell free and neuronal cell systems using the compounds at a nanomolar (nM) and/or micromolar (uM) set of concentrations. Compounds can be tested in vivo in the tg mouse, at oral and IP (parenterally administered) at nM concentrations model of PD.

A first set of experiments can comprise daily injections for 2 weeks with compounds of the invention at 1, 10 and 100 nM. Blood, CSF, brain and liver can be analyzed for levels of SYN and compound. After preliminary data is obtained then more extensive studies with groups pf 20 mice can be performed with daily injections in 3 and 6 month old mice for 3 and 6 months duration of treatment. Mice can be analyzed behaviorally, neuropathologically and biochemically for SYN aggregation and neurodegeneration. Blood and CSF can be analyzed for levels of SYN and compound. The compounds can be further refined and modified to increase permeability, access into the brain and bio-availability. The selected compounds can be first tested for toxicity in non tg mice. SYN knock out mice are viable are neurologically intact; this suggests that using a compound that blocks SYN will have low or no toxicity when tested in the SYN tg mice.

Compounds of the invention screened from these in vivo experiments can be prepared for toxicological studies and prepared for a phase I clinical trial.

The compounds of the invention comprise a novel therapy for PD, LBD, AD and MSA based on blocking neurotoxic SYN oligomerization in the cell membrane, and their efficacy can be testing using well known art-accepted animal models for PD, LBD, AD or MSA.

Figure 17:
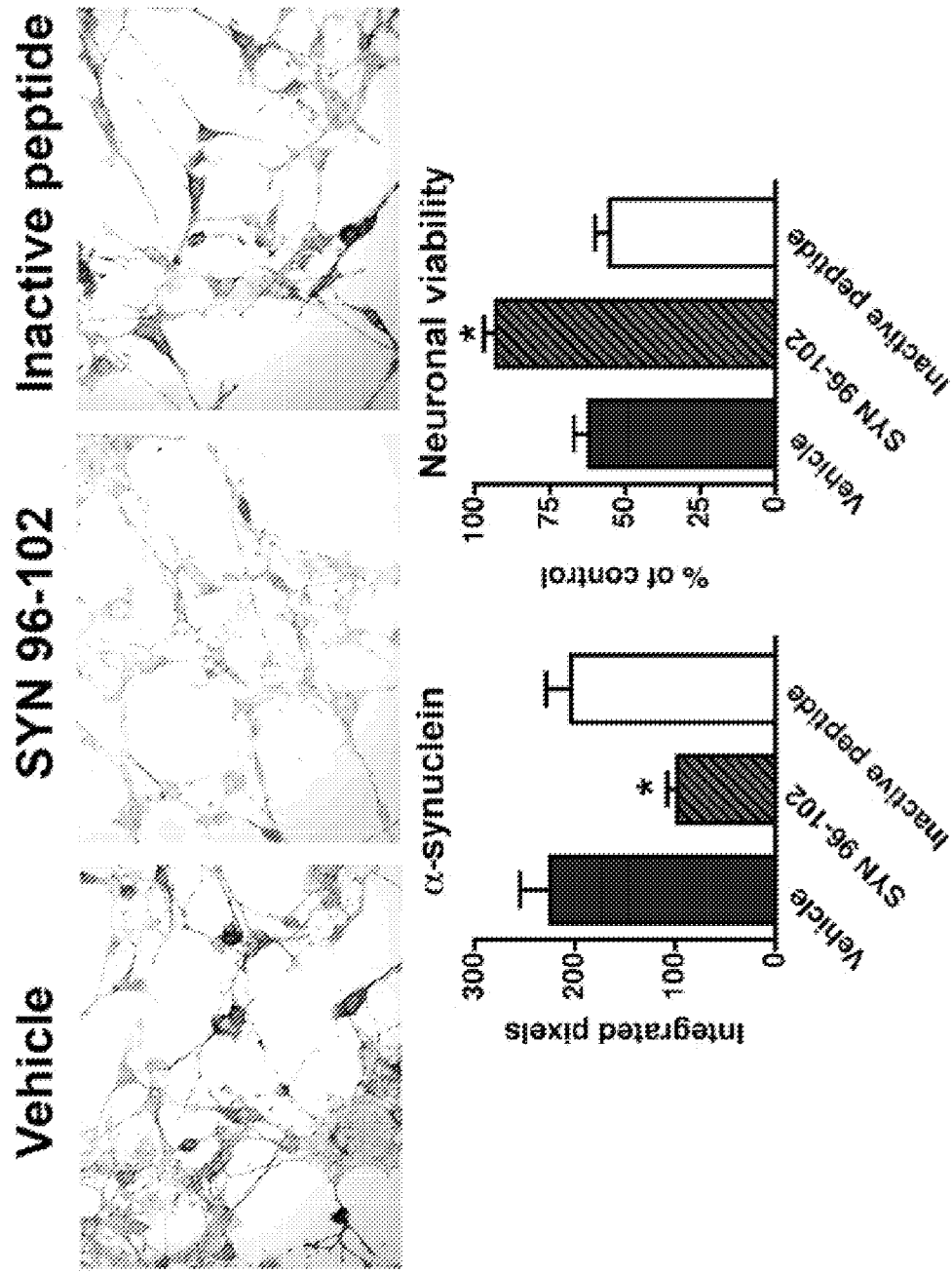
FIG. 17 illustrates the effects of a peptide blocker of α-syn aggregation of this invention in neuronal viability, as discussed in detail the Examples, below. The upper three photomicrograph panels of neuronal cultures demonstrate that overexpressing α-syn treatment for 24 hrs with the exemplary 96-102 KKDQLGK peptide (SEQ ID NO:1) of this invention at 1 uM reduced α-syn accumulation (middle upper panel), compared to inactive scrambled peptide (right-hand upper panel), or negative control (the "vehicle only" left-hand upper panel); this data graphically show in the lower left-hand graph illustration. Treatment with the 96-102 KKDQLGK (SEQ ID NO:1) peptide of this invention also improved neuronal viability as assayed by the LDH assay; this data is graphically summarized in the lower right-hand graph illustration.

FIG. 17 illustrates the effects of a peptide blocker of α-syn aggregation of this invention in neuronal viability. The upper three photomicrograph panels of neuronal cultures demonstrate that overexpressing α-syn treatment for 24 hrs with the exemplary 96-102 KKDQLGK peptide (SEQ ID NO:1) of this invention at 1 uM reduced α-syn accumulation (middle upper panel), compared to inactive scrambled peptide (right-hand upper panel), or negative control (the "vehicle only" left-hand upper panel); this data graphically show in the lower left-hand graph illustration. Treatment with the 96-102 KKDQLGK (SEQ ID NO:1) peptide of this invention also improved neuronal viability as assayed by the LDH assay; this data is graphically summarized in the lower right-hand graph illustration.

Figure 18:
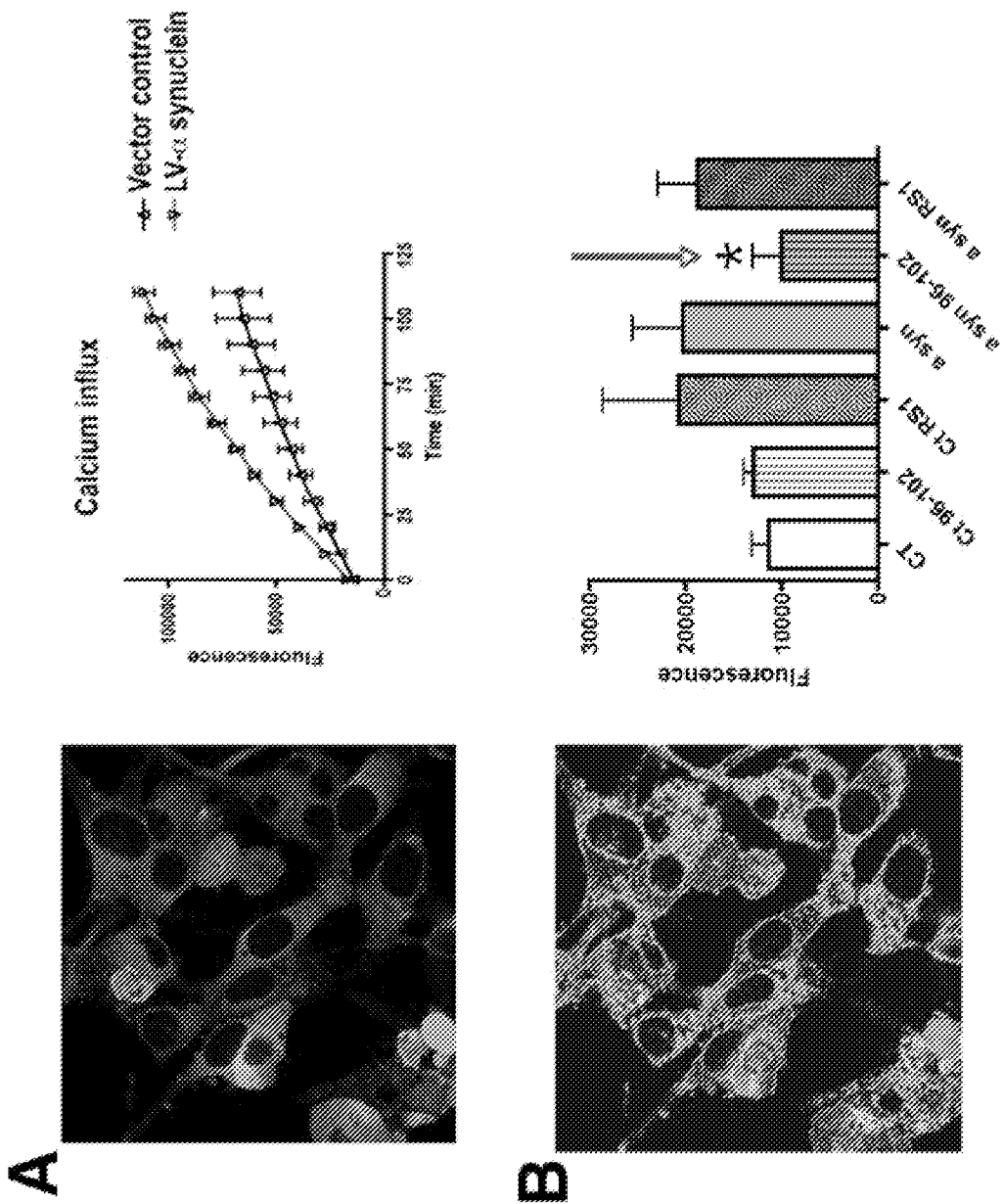
FIG. 18 illustrates the effects of a peptide blocker of α-syn aggregation of this invention in neuronal calcium levels, as discussed in detail the Examples, below.

FIG. 18 illustrates the effects of a peptide blocker of α-syn aggregation of this invention in neuronal calcium levels. FIG. 18A is a micrograph illustration showing that in neuronal cultures overexpressing α-syn there is a significant time dependent increase in intracellular calcium influx as determined by Fluo-4 and the FLIPR assay. FIG. 18B is a micrograph illustration of the neuronal cultures after treatment with the exemplary 96-102 KKDQLGK (SEQ ID NO:1) peptide of this invention, where the cultures have reduced neuronal calcium influx after 24 hrs at 37° C. (arrow) compared to vehicle and scrambled peptide controls. Data from these studies is graphically summarized on the right hand panels.

Figure 19:
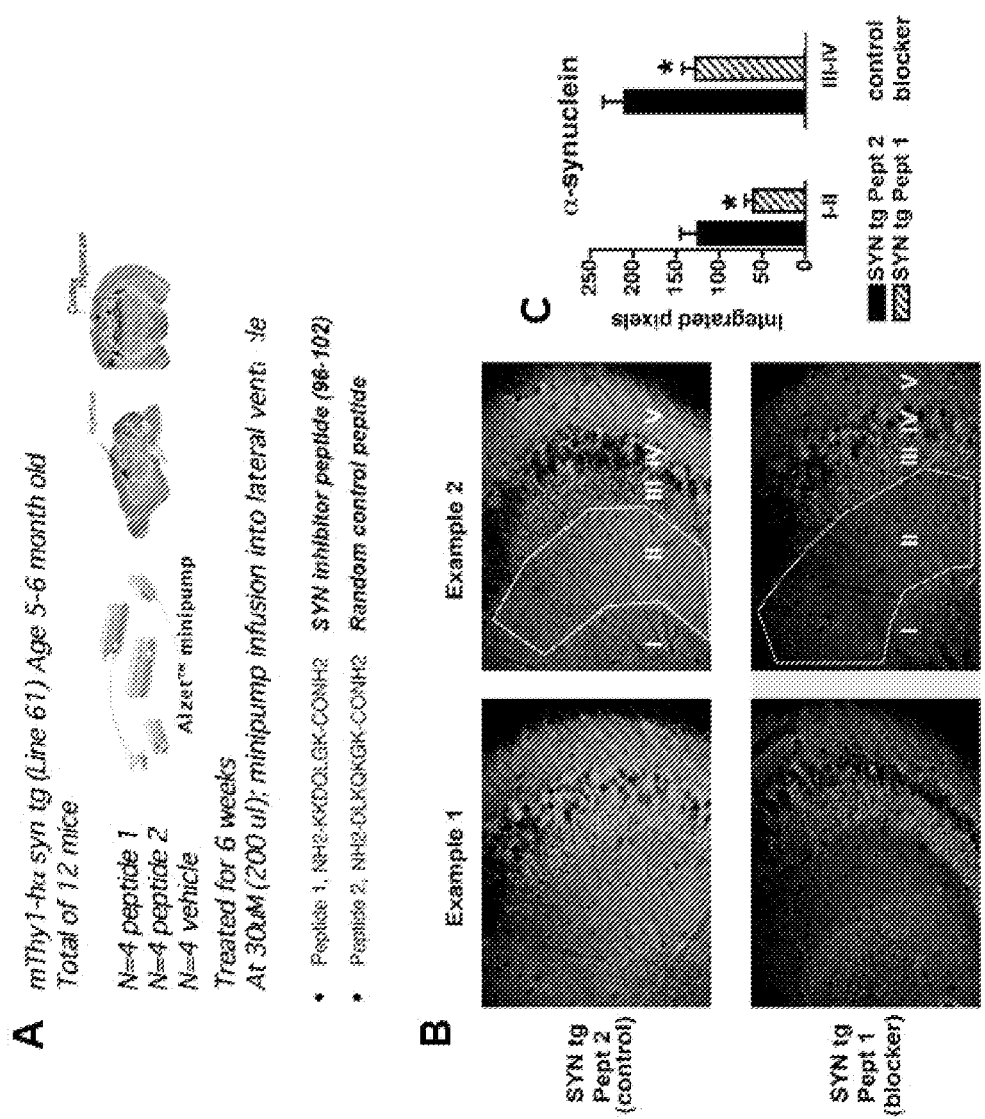
FIG. 19 illustrates the effects of peptide blocker of α-syn aggregation in vivo in α-syn (α-syn) transgenic mice, as discussed in detail the Examples, below.

FIG. 19 illustrates the effects of peptide blocker of α-syn aggregation in vivo in α-syn (α-syn) transgenic mice. FIG. 19A illustrates the experimental design: for these studies the thy1-overexpressing α-syn received intraventricular infusions with osmotic minipumps of control scrambled peptide, or the exemplary peptide of this invention 96-102 KKDQLGK (SEQ ID NO:1) for 6 weeks, at 30 μM peptide, where 200 μl of solution is minipumped into the lateral ventricle of the animal. FIG. 19B is a micrograph illustrating that infusion of the exemplary peptide of this invention, the 96-102 KKDQLGK (SEQ ID NO:1) peptide, resulted in a significant reduction in neuronal α-syn accumulation in the hippocampus, as compared to scrambled peptide controls; and FIG. 19C graphically summarizes this data (where "blocker" is the 96-102 KKDQLGK (SEQ ID NO:1) peptide).

Figure 20:
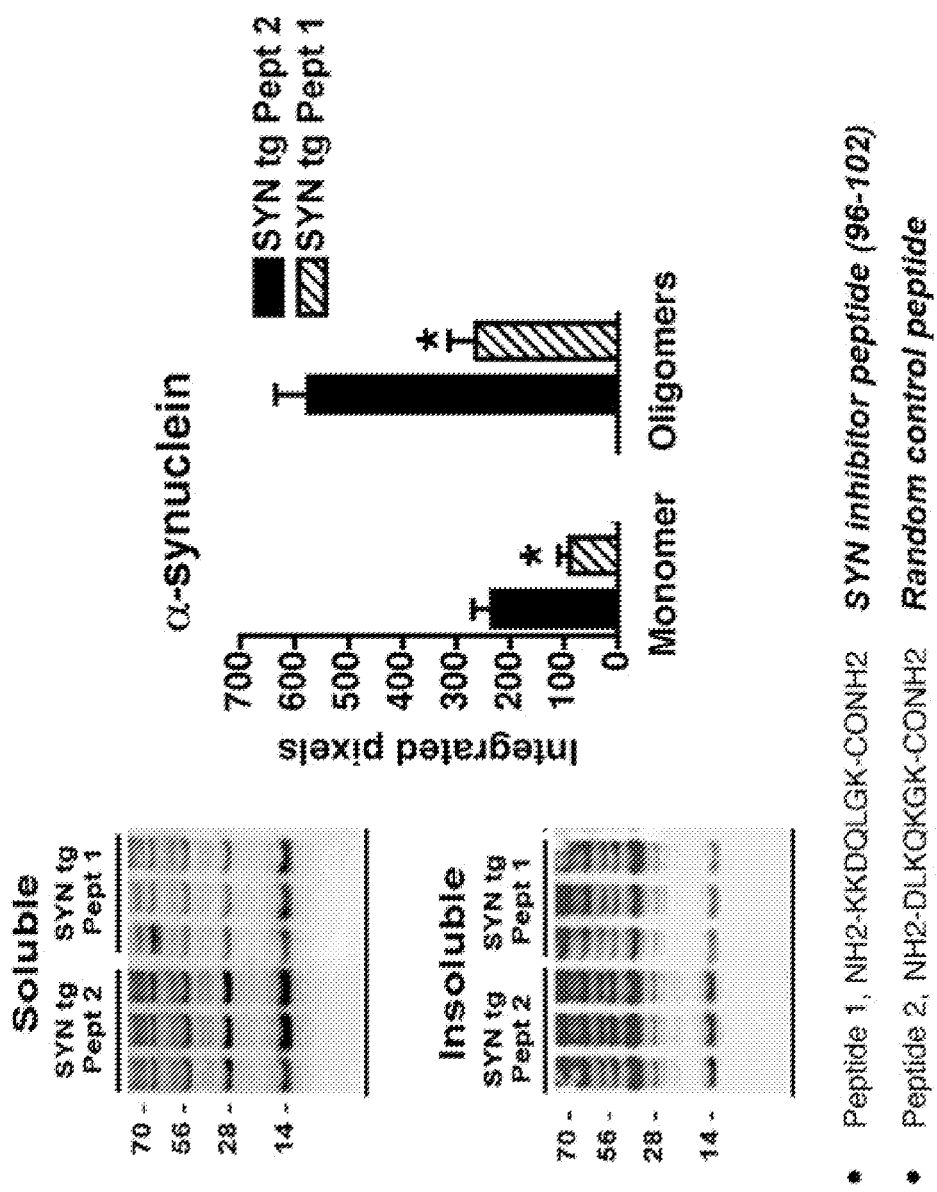
FIG. 20 illustrates immunoblot analyses (left-hand panels) that demonstrate that an exemplary α-syn (α-syn) peptide blocker of the invention is effective in vivo in α-syn (α-syn) transgenic mice, as discussed in detail the Examples, below. Infusion of the exemplary 96-102 KKDQLGK (SEQ ID NO:1) peptide of this invention resulted in a significant reduction in the levels of monomeric and aggregated α-syn accumulation compared to scrambled peptide controls; this data is graphically summarized in the right hand panel.

FIG. 20 illustrates immunoblot analyses (left-hand panels) that demonstrate that an exemplary α-syn (α-syn) peptide blocker of the invention is effective in vivo in α-syn (α-syn) transgenic mice. Infusion of the exemplary 96-102 KKDQLGK (SEQ ID NO:1) peptide of this invention resulted in a significant reduction in the levels of monomeric and aggregated α-syn accumulation compared to scrambled peptide controls; the data is graphically summarized in the right hand panel.

A number of embodiments of the invention have been described. Nevertheless, it will be understood that various modifications may be made without departing from the spirit and scope of the invention. Accordingly, other embodiments are within the scope of the following claims.

What is claimed is:

1. A compound comprising
(1) (a) formula (II)

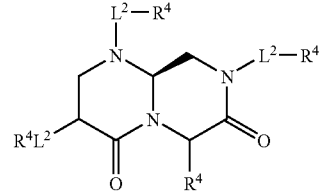

(II)

wherein each $L^2$ is independently selected from a group consisting of a bond, $SO_2$, $SO_2NH$, $CO_2NH$, (C=O)NH, (C=O)NHNH(C=O), C=O, O(C=O), (C=O)O and C1-C22 alkylene, each $R^4$ is independently selected from a group consisting of H, C1-C6 aminoalkyl, C2-C6 aminoalkenyl, C2-C6 aminoalkynyl, C1-C6 alkyl, C2-C6 alkenyl, C2-C6 alkynyl and 5-6 membered aromatic ring;

and wherein at least one $R^4$ is a C1-C6 aminoalkyl.

2. A pharmaceutical formulation or pharmaceutical composition comprising:
(a) at least one compound of claim 1.

3. A liposome comprising:
(a) at least one compound of claim 1; or,
(b) compound comprising a formula (II)

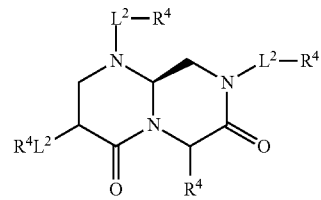

(II)

SEQUENCE LISTING

```
<160> NUMBER OF SEQ ID NOS: 2

<210> SEQ ID NO 1
<211> LENGTH: 7
<212> TYPE: PRT
<213> ORGANISM: artificial sequence
<220> FEATURE:
<223> OTHER INFORMATION: synthetic peptide

<400> SEQUENCE: 1

Lys Lys Asp Gln Leu Gly Lys
1               5

<210> SEQ ID NO 2
<211> LENGTH: 9
<212> TYPE: PRT
<213> ORGANISM: artificial sequence
<220> FEATURE:
<223> OTHER INFORMATION: synthetic peptide

<400> SEQUENCE: 2

Glu Lys Thr Lys Glu Gln Val Thr Asn
1               5
``` wherein each $L^2$ is independently selected from a group consisting of a bond, $SO_2$, $SO_2NH$, $CO_2NH$, (C=O)NH, (C=O)NHNH(C=O), C=O, O(C=O), (C=O)O and C1-C22 alkylene, and each $R^4$ is independently selected from a group consisting of H, C1-C6 aminoalkyl, C2-C6 aminoalkenyl, C2-C6 aminoalkynyl, C1-C6 alkyl, C2-C6 alkenyl, C2-C6 alkynyl and 5-6 membered aromatic ring.

4. A nanoparticle comprising at least one compound of claim 1.

5. A kit comprising at least one compound of claim 1.

6. A compound formulated as a pharmaceutically acceptable salt of a compound, wherein the compound comprises a formula (II)

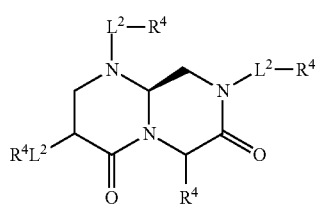

(II)

wherein each $L^2$ is independently selected from a group consisting of a bond, $SO_2$, $SO_2NH$, $CO_2NH$, (C=O)NH, (C=O)NHNH(C=O), C=O, O(C=O), (C=O)O and C1-C22 alkylene, each $R^4$ is independently selected from a group consisting of H, C1-C6 aminoalkyl, C2-C6 aminoalkenyl, C2-C6 aminoalkynyl, C1-C6 alkyl, C2-C6 alkenyl, C2-C6 alkynyl and 5-6 membered aromatic ring;

and wherein at least one $R^4$ is a C1-C6 aminoalkyl.

7. A composition comprising a polypeptide or peptide or a non-protein moiety and a compound of claim 1.

8. The composition of claim 7, wherein the non-protein moiety and/or the polypeptide or peptide, is conjugated to a carrier.

9. The compound of claim 8, wherein the carrier comprises or consists of a poly-Arg, a TAT or a *Drosophila antennapedia* homeodomain.

10. A composition comprising a compound of claim 1 in an aqueous solution or suspension.

11. The liposome of claim 3, wherein the liposome comprises a multilayered liposome.

12. The liposome of claim 3, wherein the liposome comprises a compound comprising a formula (II)

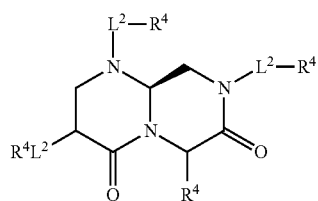

(II)

wherein each $L^2$ is independently selected from a group consisting of a bond, $SO_2$, $SO_2NH$, $CO_2NH$, (C=O)NH, (C=O)NHNH(C=O), C=O, O(C=O), (C=O)O and C1-C22 alkylene, and each $R^4$ is independently selected from a group consisting of H, C1-C6 aminoalkyl, C2-C6 aminoalkenyl, C2-C6 aminoalkynyl, C1-C6 alkyl, C2-C6 alkenyl, C2-C6 alkynyl and 5-6 membered aromatic ring.

13. The pharmaceutical formulation or pharmaceutical composition of claim 2, formulated as an aqueous suspension, a solid, a liquid, a powder, an emulsion, a lyophilized powder, a spray, a cream, a lotion, a controlled release formulation, a tablet, a pill, a gel, a liposome, on a patch, in an implant, on a tape, a dragee, a capsule, a lozenge, a gel, a syrup, a slurry and/or a suspension.

* * * * *